(12) United States Patent
Meguro

(10) Patent No.: US 11,600,385 B2
(45) Date of Patent: Mar. 7, 2023

(54) MEDICAL IMAGE PROCESSING DEVICE, ENDOSCOPE SYSTEM, DIAGNOSIS SUPPORT METHOD, AND PROGRAM

(71) Applicant: FUJIFILM Corporation, Tokyo (JP)

(72) Inventor: Misaki Meguro, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 308 days.

(21) Appl. No.: 17/111,514

(22) Filed: Dec. 4, 2020

(65) Prior Publication Data
US 2021/0192738 A1 Jun. 24, 2021

(30) Foreign Application Priority Data
Dec. 24, 2019 (JP) .............................. JP2019-233104

(51) Int. Cl.
*G16H 40/67* (2018.01)
*G06T 7/00* (2017.01)
(Continued)

(52) U.S. Cl.
CPC ......... *G16H 40/67* (2018.01); *A61B 1/00045* (2013.01); *A61B 1/000094* (2022.02); *A61B 1/000096* (2022.02); *G06N 3/08* (2013.01); *G06T 7/0016* (2013.01); *G06T 7/70* (2017.01); *G16H 30/40* (2018.01); *A61B 1/04* (2013.01);
(Continued)

(58) Field of Classification Search
CPC ......... G16H 40/67; G06T 7/70; G06T 7/0016; G06T 2207/10068; G06T 2207/20084; G06T 2207/30096; G06H 30/40; A61B 1/000094; A61B 1/000096; A61B 1/00045; A61B 1/04; A61B 1/273; G06N 3/08; G06F 3/14
See application file for complete search history.

(56) References Cited

U.S. PATENT DOCUMENTS

| 2014/0158898 A1* | 6/2014 | Akagi ................... A61B 6/542 |
| | | 250/394 |
| 2015/0080652 A1* | 3/2015 | Staples, II ............. G16H 30/40 |
| | | 600/109 |

(Continued)

FOREIGN PATENT DOCUMENTS

| JP | 2019169049 | 10/2019 |
| WO | 2018105063 | 6/2018 |

*Primary Examiner* — Vu Le
*Assistant Examiner* — Julius Chai
(74) *Attorney, Agent, or Firm* — JCIPRNET

(57) ABSTRACT

There are provided a medical image processing device, and endoscope system, a diagnosis support method, and a program which can support diagnosis by avoiding an inappropriate report in a case where any of site information of an observation target and lesion type information detected from a medical image is incorrect.

The medical image processing device includes at least one processor. The at least one processor acquires the medical image, acquires the site information indicating a site of an observation target included in the medical image, in a human body, detects a lesion from the medical image to acquire the lesion type information indicating a lesion type, determines presence or absence of a contradiction between the site information and the lesion type information, and decides a report mode of the site information and the lesion type information on the basis of a determination result.

20 Claims, 12 Drawing Sheets

(51) Int. Cl.
*G06T 7/70* (2017.01)
*A61B 1/00* (2006.01)
*G16H 30/40* (2018.01)
*G06N 3/08* (2006.01)
*A61B 1/04* (2006.01)
*G06F 3/14* (2006.01)
*A61B 1/273* (2006.01)

(52) U.S. Cl.
CPC ................ *A61B 1/273* (2013.01); *G06F 3/14* (2013.01); *G06T 2207/10068* (2013.01); *G06T 2207/20084* (2013.01); *G06T 2207/30096* (2013.01)

(56) References Cited

U.S. PATENT DOCUMENTS

| | | |
|---|---|---|
| 2019/0295248 A1 | 9/2019 | Nakamura et al. |
| 2019/0311476 A1 | 10/2019 | Hayami et al. |
| 2020/0337537 A1* | 10/2020 | Hirasawa ............... A61B 1/045 |

* cited by examiner

| ESOPHAGUS | BARRETT'S ADENOCARCINOMA |
| --- | --- |
| | SQUAMOUS CELL CARCINOMA |
| | ESOPHAGEAL HIATUS HERNIA |
| | REFLUX ESOPHAGITIS |
| STOMACH | STOMACH CANCER |
| | GASTRIC ULCER |
| | HYPERPLASTIC POLYP |
| | FUNDIC GLAND POLYP | ns
MEDICAL IMAGE PROCESSING DEVICE, ENDOSCOPE SYSTEM, DIAGNOSIS SUPPORT METHOD, AND PROGRAM

CROSS-REFERENCE TO RELATED APPLICATIONS

The present application claims priority under 35 U.S.C. § 119 to Japanese Patent Application No. 2019-233104 filed on Dec. 24, 2019. The above application is hereby expressly incorporated by reference, in its entirety, into the present application.

BACKGROUND OF THE INVENTION

1. Field of the Invention

The present invention relates to a medical image processing device, an endoscope system, a diagnosis support method, and a program.

2. Description of the Related Art

In recent years, in the field of medical images such as endoscopic images, artificial intelligence (AI) technology or the like is introduced to recognize the position of a lesion and/or the type of a lesion using image analysis, and technology for supporting diagnosis by reporting the recognition result has been developed. In a process for recognizing a lesion or the like, an AI module is used which includes an inference model learned by machine learning including deep learning.

WO2018/105063A discloses an endoscope device which detects a lesion part from an endoscopic image obtained by an endoscope and performs discrimination and classification of the lesion part. A processor in the endoscope device disclosed in WO2018/105063A includes a discrimination support unit that is a circuit performing various kinds of processing for discrimination support. The discrimination support unit includes a lesion region specifying unit that specifies a region of a lesion part from the endoscopic image, and an organ site estimation unit that estimates a site of an organ as an observation target based on the endoscopic image. A classifier using machine learning is applied to the lesion region specifying unit and the organ site estimation unit. The discrimination support in WO2018/105063A is understood as a term corresponding to the diagnosis support in this specification.

Further, JP2019-169049A discloses a medical information system including a computer that extracts a specific region and discriminates the type of a lesion using a neural network learned using a deep learning method.

SUMMARY OF THE INVENTION

In an examination using medical images such as an endoscope examination, lesion detection by deep learning or the like is effective in diagnosis support for a doctor. For example, in a case of an endoscope examination of an upper digestive organ, since the esophagus, the stomach, and the duodenum are observed by a series of examinations, it is desired to perform a report by combining site information of an observation target and lesion type information indicating the lesion type detected from the image.

On the other hand, it cannot be said that the recognition performance of images by deep learning or the like is perfect, and there is a possibility that a miss (error) may occur in the recognition result output from the AI. In particular, in a case of respectively performing site recognition and lesion recognition using separate and independent methods, in a case where a miss occurs in any recognition result, there may be a contradiction between the site information and the lesion type information reported on a screen of a monitor.

Further, in the lesion detection by deep learning or the like, different AI modules may be prepared for each target site, and in such a system, it is conceivable to switch detection methods according to the observation target site. For example, it is conceivable to construct a system in which AI modules using a different inference model for each site such as the esophagus, the stomach, and the duodenum are prepared, and switching to a detector (AI module) suitable for detecting a lesion in each site is performed in conjunction with the site recognition. As described above, since different sites are observed in a series of endoscope examinations in which a plurality of sites are the examination targets, it is required to automatically switch a detection method according to the observation target site.

However, for example, in a case where a miss (error) has occurred in site recognition, there is a possibility that the system may behave unintentionally.

The problem described above is not limited to the endoscope examination, and is a common problem expected in a case where acquisition of site information of an observation target from various medical images and acquisition of lesion type information based on the medical image are performed.

The invention is made in view of such circumstances and solves at least one problem among the plurality of problems, and an object of the invention is to provide a medical image processing device, an endoscope system, a diagnosis support method, and a program which can support diagnosis by avoiding an inappropriate report in a case where any of the site information of the observation target and the lesion type information indicating the lesion type detected from the medical image is incorrect.

A medical image processing device according to an aspect of the present disclosure has at least one processor, in which the at least one processor acquires a medical image, acquires site information indicating a site of an object shown in the medical image, in a human body, detects a lesion from the medical image to acquire lesion type information indicating a lesion type, determines presence or absence of a contradiction between the site information and the lesion type information, and decides a report mode of the site information and the lesion type information on the basis of a determination result.

Determining the presence or absence of a contradiction between the site information and the lesion type information may be understood as determining the consistency between the site information and the lesion type information. The correspondence relationship between the sites and the candidates of the lesion type that may be detected in each site may be specified from the medical knowledge. The at least one processor can control the report mode in which a report to avoid a report of contradicting information is performed by determining whether there is a contradiction between the site information and the lesion type information. The report mode may be referred to as a report method. According to the aspect, it is possible to take measures such as avoiding a situation in which contradicting information is reported, to provide information useful for diagnosis and the like.

The medical image processing device may be configured as a single device or may be configured by combining a plurality of devices. For example, the medical image processing device may be realized using one or a plurality of computers. The "device" includes the concepts of a "system" and a "module".

The medical image processing device according to the aspect of the present disclosure may further comprise a memory, in which in the memory, a table representing a correspondence relationship between a plurality of types of sites and lesion types for each site may be stored, and the at least one processor may determine presence or absence of a contradiction between the site information and the lesion type information using the table.

The "table" can be created on the basis of the medical knowledge. The at least one processor can determine whether the acquired combination of the site information and the lesion type information is a combination described in the table, determine that "there is no contradiction" in a case where the acquired combination corresponds to the combination described in the table, and determine that "there is a contradiction" in a case where the acquired combination does not correspond to the combination described in the table.

In the medical image processing device according to the aspect of the present disclosure, in the memory, a command executed by the at least one processor may be stored, and the at least one processor may perform processing including acquisition of the medical image, acquisition of the site information, acquisition of the lesion type information, determination of presence or absence of the contradiction, and decision of the report mode by executing the command by the at least one processor.

In the medical image processing device according to the aspect of the present disclosure, the at least one processor may decide that both the site information and the lesion type information are reported in a case where it is determined that there is no contradiction between the site information and the lesion type information.

In the medical image processing device according to the aspect of the present disclosure, the at least one processor may decide that at least one of the site information or the lesion type information is not reported in a case where it is determined that there is a contradiction between the site information and the lesion type information.

In the medical image processing device according to the aspect of the present disclosure, in a case where it is determined that there is a contradiction between the site information and the lesion type information, the at least one processor may compare a reliability of the site information with a reliability of the lesion type information, and decide to report the information with a higher reliability and not to report the information with a lower reliability of the site information and the lesion type information.

In the medical image processing device according to the aspect of the present disclosure, in a case where it is determined that there is a contradiction between the site information and the lesion type information, the at least one processor may decide not to report the site information and decide to report the lesion type information.

In the medical image processing device according to the aspect of the present disclosure, in a case where it is determined that there is a contradiction between the site information and the lesion type information, the at least one processor may compare each of a reliability of the site information and a reliability of the lesion type information with a reference value, and decide not to report both the site information and the lesion type information in a case where both the reliability of the site information and the reliability of the lesion type information are equal to or less than the reference value.

In the medical image processing device according to the aspect of the present disclosure, in a case where it is determined that there is a contradiction between the site information and the lesion type information, the at least one processor may decide to report that the contradiction has occurred.

In the medical image processing device according to the aspect of the present disclosure, the at least one processor may acquire the site information by recognizing the site of the object from the medical image.

The term "recognition" includes the concepts of identification, discrimination, inference, estimation, detection, classification, and the like. The at least one processor may perform recognition processing using a learned model that has acquired recognition performance by machine learning, for example.

In the medical image processing device according to the aspect of the present disclosure, the at least one processor may acquire the site information indicated by an inference result that is output from a first neural network by inputting the medical image to the first neural network, and acquire the lesion type information of the lesion present in the medical image by inference using an inference result that is output from a second neural network by inputting the medical image to the second neural network.

In the medical image processing device according to the aspect of the present disclosure, the at least one processor may acquire a score indicating a reliability of the site information using the first neural network, and acquire a score indicating a reliability of the lesion type information using the second neural network.

In the medical image processing device according to the aspect of the present disclosure, the at least one processor may further generate a report control signal for realizing a report of the decided report mode.

In the medical image processing device according to the aspect of the present disclosure, the report control signal may include a display signal for realizing a report by display using a display.

The medical image processing device according to the aspect of the present disclosure may further comprise the display that performs display of information according to the report mode decided by the at least one processor.

In the medical image processing device according to the aspect of the present disclosure, the at least one processor may acquire the time-series medical image.

The time-series medical image may be a video, or may be an image group captured at specific time intervals, such as continuous imaging or interval imaging. Further, the time interval of imaging in a time-series manner may not necessarily be constant.

The medical image may be an endoscopic image captured using an endoscope. The endoscope may be an endoscope scope or a capsule endoscope.

In the medical image processing device according to the aspect of the present disclosure, the site may be an organ, and the site information may be information indicating a name of the organ.

An endoscope system according to another aspect of the present disclosure comprises an endoscope scope; and at least one processor, in which the at least one processor acquires an endoscopic image obtained by imaging an inside of a body using the endoscope scope, acquires site information indicating a site of an object shown in the endoscopic image, in a human body, detects a lesion from the endoscopic image to acquire lesion type information indicating a lesion type, determines presence or absence of a contradiction between the site information and the lesion type information, decides a report mode of the site information and the lesion type information on the basis of a determination result, and generates a report control signal for executing a report according to the decided report mode.

A diagnosis support method according to still another aspect of the present disclosure is a diagnosis support method performed by at least one processor, and includes acquiring a medical image; acquiring site information indicating a site of an observation target included in the medical image, in a human body; detecting a lesion from the medical image to acquire lesion type information indicating a lesion type; determining presence or absence of a contradiction between the site information and the lesion type information; deciding a report mode of the site information and the lesion type information on the basis of a determination result; and displaying information on a display according to the decided report mode.

A program according to still another aspect of the present disclosure causes a computer to realize a function of acquiring a medical image; a function of acquiring site information indicating a site of an object shown in the medical image, in a human body; a function of detecting a lesion from the medical image to acquire lesion type information indicating a lesion type; a function of determining presence or absence of a contradiction between the site information and the lesion type information; and a function of deciding a report mode of the site information and the lesion type information on the basis of a determination result.

According to the invention, it is possible to take measures such as avoiding a situation in which contradicting information is reported in a case where there is a contradiction between the site information of the observation target and the lesion type information detected from the medical image, and to provide information useful for diagnosis and the like by realizing an appropriate report.

DESCRIPTION OF THE PREFERRED EMBODIMENTS

Figure 1:
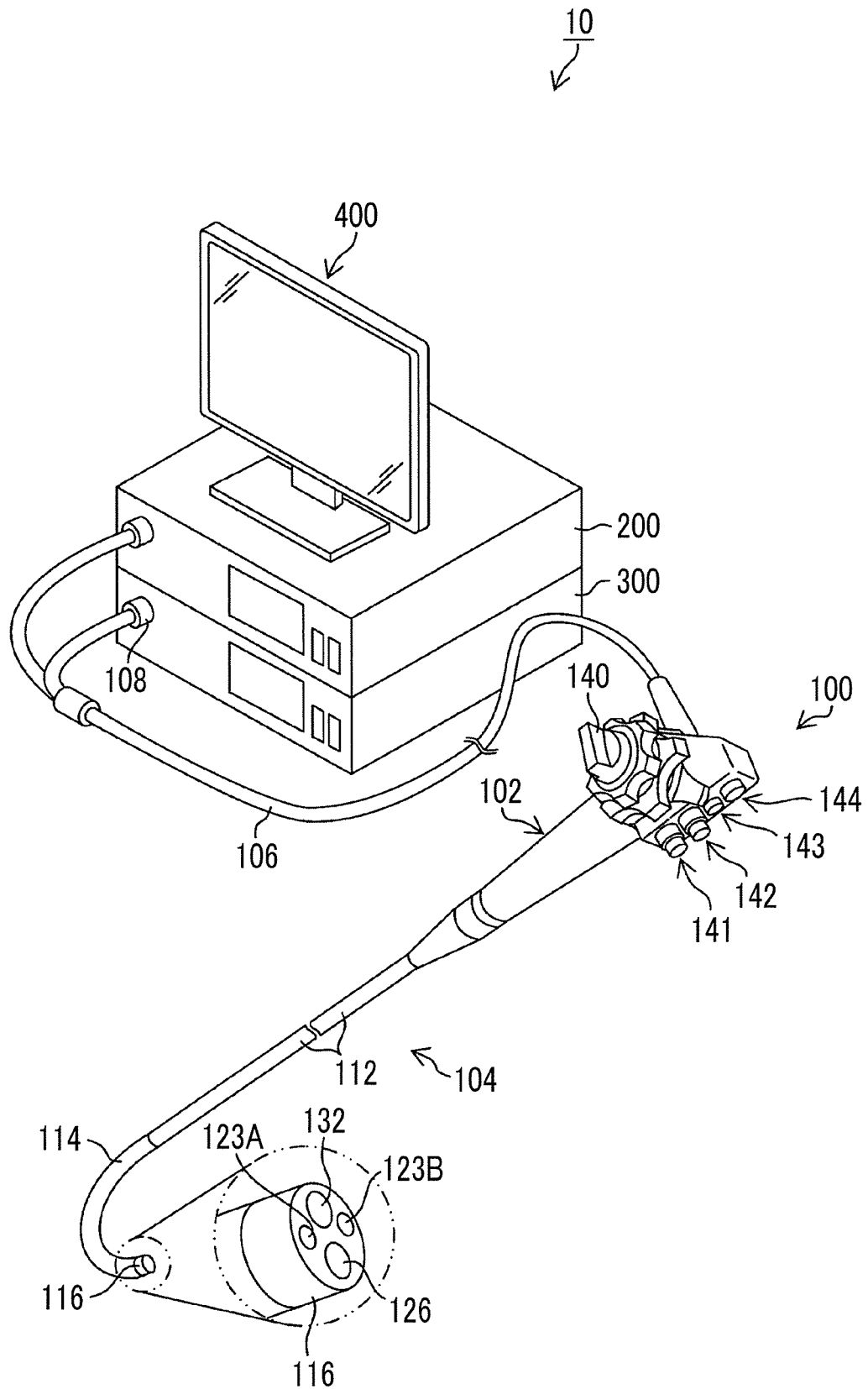
FIG. 1 is a perspective diagram illustrating an example of the appearance of an endoscope system according to an embodiment of the invention.

Hereinafter, preferred embodiments of the invention will be described in detail with reference to the accompanying drawings. In the specification, the same constituents are denoted by the same reference numerals, and the redundant description will be omitted as appropriate.

Outline of Endoscope System

FIG. 1 is a perspective diagram illustrating an example of the appearance of an endoscope system 10 according to an embodiment of the invention. The endoscope system 10 comprises an endoscope scope 100, a processor device 200, a light source device 300, and a monitor 400.

The endoscope scope 100 is an electronic endoscope, and is a flexible endoscope, for example. The endoscope scope 100 comprises a hand operation part 102, an insertion part 104, and a universal cable 106. The hand operation part 102 comprises an angle knob 140, an air/water supply button 141, a suction button 142, a function button 143, and an imaging button 144.

The angle knob 140 is used in a bending operation instructing a bending direction and a bending amount of a bendable portion 114 in the insertion part 104. The angle knob 140 includes two kinds of knobs, an up-down angle knob for bending the bendable portion 114 in an up-down direction and a left-right angle knob for bending the bendable portion 114 in a left-right direction.

The air/water supply button 141 accepts operations of an air supply instruction and a water supply instruction. The suction button 142 accepts an operation of a suction instruction. Various functions are assigned to the function button 143. The function button 143 accepts an instruction operation of various functions. The imaging button 144 accepts an imaging instruction operation. The term "imaging" includes the concepts of both the capturing of a static image and the capturing of a video. The imaging instruction operation includes an operation instructing an imaging timing of a static image, and an operation instructing an imaging start timing and an imaging end timing of a video.

A user operates the endoscope scope 100 by gripping the hand operation part 102, inserts the insertion part 104 into the inside of a subject, and observes the inside of the subject.

Here, the "user" refers to a doctor as an operator. The description of "subject" is synonymous with a patient, an examinee, or a subject to be examined.

The insertion part 104 is a part to be inserted into the inside of the subject. The insertion part 104 is provided to be continuous to the hand operation part 102, and comprises a soft portion 112, the bendable portion 114, and a hard distal end portion 116 that are arranged in this order from the hand operation part 102.

The soft portion 112 is a flexible portion provided between the hand operation part 102 and the bendable portion 114. The bendable portion 114 is a portion including a mechanism that is bendable by the operation of the hand operation part 102. In a case where the user operates the angle knob 140, the user can bend the bendable portion 114 to vertically and laterally change the direction of the hard distal end portion 116.

In FIG. 1, a part of the hard distal end portion 116 is illustrated in an enlarged manner. The hard distal end portion 116 is provided with an imaging unit including an imaging lens 132, an illumination unit including illumination lenses 123A and 123B, and a forceps port 126. The imaging unit is illustrated with reference numeral 130 in FIG. 2. Further, the illumination unit is illustrated with reference numeral 123 in FIG. 2.

In the observation and treatment, white light and/or narrow-band light can be emitted via the illumination lenses 123A and 123B according to the user's operation. The narrow-band light includes at least one of red narrow-band light, green narrow-band light, blue narrow-band light, or violet narrow-band light.

In a case where the air/water supply button 141 is operated, cleaning water is ejected from a water supply nozzle (not illustrated) or gas is ejected from an air supply nozzle (not illustrated). The cleaning water and gas can be used in cleaning the imaging lens 132, the illumination lenses 123A and 123B, and the like. The water supply nozzle and the air supply nozzle may be shared.

The forceps port 126 communicates with a treatment tool insertion passage (not illustrated) disposed inside the insertion part 104. A treatment tool (not illustrated) is inserted into the treatment tool insertion passage. A treatment tool inlet (not illustrated) for introducing the treatment tool into the treatment tool insertion passage is provided in the hand operation part 102. As the treatment tool, for example, biopsy forceps, a catheter, or a high-frequency snare may be used. Further, in the treatment tool, a guide tube, a trocar tube, a sliding tube, and the like are included. The treatment tool is supported in the treatment tool insertion passage to be appropriately moved forwards and backwards. In the tumor removal and the like, the user can perform a necessary treatment on the subject using the treatment tool.

The universal cable 106 is a cable for connecting the endoscope scope 100 to the processor device 200 and the light source device 300. An electric cable and a light guide provided to extend from the insertion part 104 are inserted into the universal cable 106. In the electric cable, a communication cable used in the signal transmission and a power supply cable used in power supply are included. The endoscope scope 100 is connected to the processor device 200 and the light source device 300 via the universal cable 106.

As the input device for inputting an instruction and the like from the user, the endoscope system 10 may comprise a foot switch and/or a sound input device (not illustrated) and the like in addition to the hand operation part 102. The foot switch comprises a pedal and a cable. The cable of the foot switch is connected to the processor device 200.

Configuration Example of Endoscope System

Figure 2:
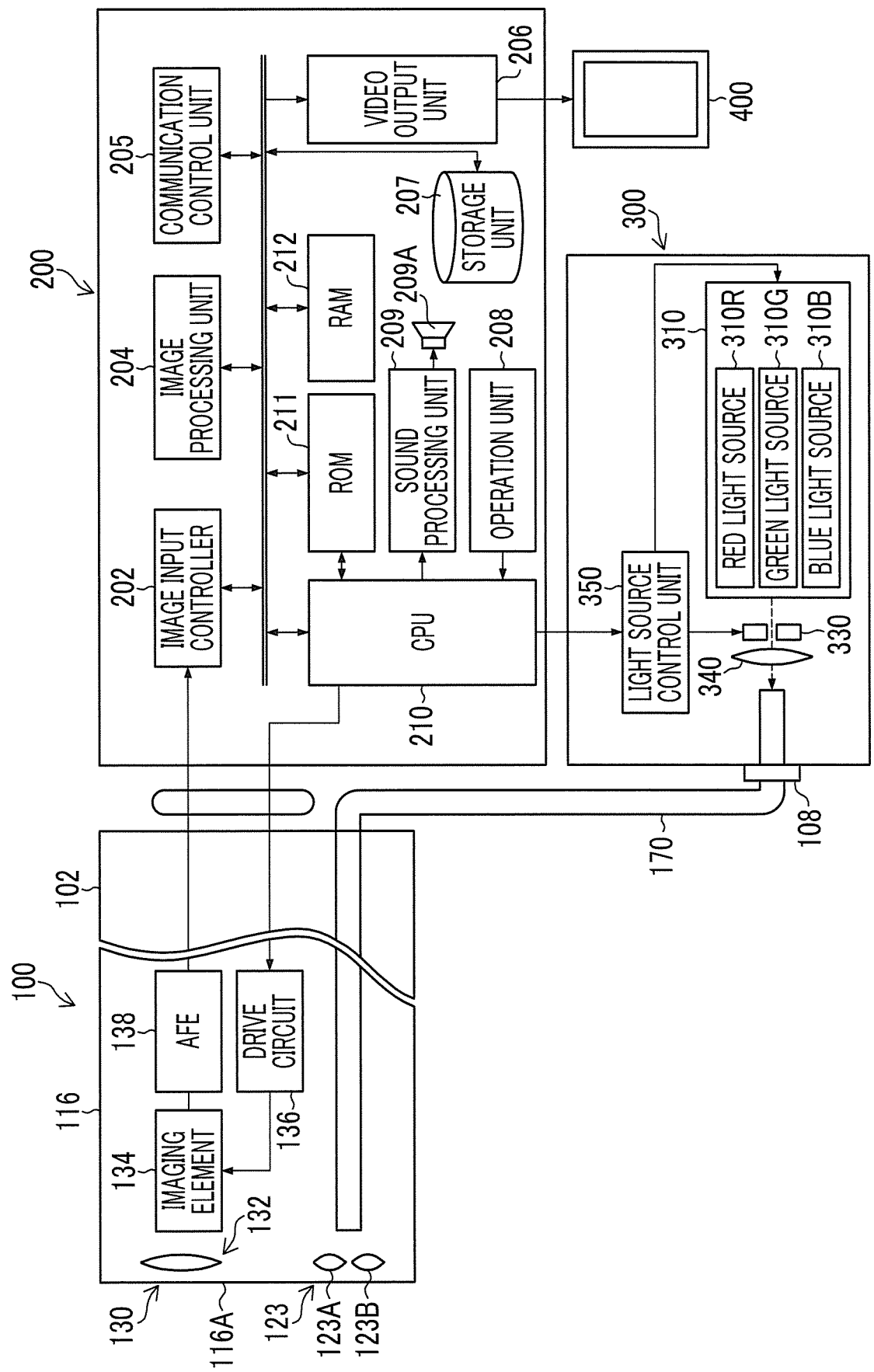
FIG. 2 is a block diagram illustrating a configuration example of the endoscope system.

FIG. 2 is a block diagram illustrating a configuration example of the endoscope system 10. Hereinafter, respective configuration examples will be described in the order of the endoscope scope 100, the light source device 300, and the processor device 200.

Description of Endoscope Scope

The endoscope scope 100 comprises the imaging unit 130 and the illumination unit 123. The imaging unit 130 is disposed inside the hard distal end portion 116. The imaging unit 130 comprises an imaging optical system including the imaging lens 132, an imaging element 134, a drive circuit 136, an analog front end (AFE) 138.

The imaging lens 132 is disposed on a distal end-side end face 116A of the hard distal end portion 116. The imaging element 134 is disposed in the back (position closer to the bendable portion 114 than the distal end-side end face 116A) of the imaging lens 132. The imaging element 134 is a complementary metal oxide semiconductor (CMOS) type image sensor, for example. As the imaging element 134, a charge coupled device (CCD) type image sensor may be applied.

The imaging element 134 is a color image pickup element, for example, and a plurality of pixels formed of a plurality of light-receiving elements comprising color filters (not illustrated) are two-dimensionally arranged in a specific pattern array on a light-receiving surface (imaging surface) of the imaging element 134. Each pixel of the imaging element 134 includes a microlens, a color filter, and a photoelectric conversion part (photodiode or the like). As the color filter, color filters of primary colors including red (R), green (G), and blue (B) are used. The arrangement form of the color pattern of the color filters is not particularly limited, and may be a Bayer array, for example.

Further, the imaging element 134 may include pixels comprising a violet color filter corresponding to a violet light source (not illustrated) and/or an infrared filter corresponding to an infrared light source (not illustrated).

The drive circuit 136 supplies various kinds of timing signals required for the operation of the imaging element 134 to the imaging element 134 on the basis of control signals transmitted from the processor device 200.

An optical image of an object as the observation target is formed on a light-receiving surface of the imaging element 134 via the imaging lens 132. The imaging element 134 converts the optical image of the object into electric signals. The electric signals output from the imaging element 134 are subjected to the processing by the analog front end 138 and converted to digital image signals.

The analog front end 138 comprises an amplifier, a filter, and an analog-digital converter. The analog front end 138 performs amplification, noise removal, analog-digital conversion, and the like on the signals output from the imaging element 134. The signals output from the analog front end 138 are sent to the processor device 200. The imaging element 134, the drive circuit 136, and the analog front end 138 may be configured as a monolithic integrated circuit, and these circuit elements can be mounted on one imaging chip.

The illumination unit 123 comprises the illumination lenses 123A and 123B. The illumination lenses 123A and 123B are disposed on the distal end-side end face 116A of the hard distal end portion 116 so as to be positioned adjacent to the imaging lens 132. An emitting end of a light guide 170 is disposed in the back of the illumination lenses 123A and 123B.

The light guide 170 is inserted into the insertion part 104, the hand operation part 102, and the universal cable 106 illustrated in FIG. 1. An incident end of the light guide 170 is disposed inside a light guide connector 108 provided to an end portion of the universal cable 106.

Description of Light Source Device

The light source device 300 supplies illumination light to the light guide 170 via the light guide connector 108. As the illumination light, light in various wavelength ranges is selected according to the observation purpose, such as white light (light in white-light wavelength range or light in a plurality of wavelength ranges) or light in one or a plurality of specific wavelength ranges, or a combination thereof. The specific wavelength range is a range narrower than the white-light wavelength range. The illumination light emitted to an observation range may be called observation light.

The light source device 300 comprises a light source 310 for illumination, a stop 330, a condenser lens 340, and a light source control unit 350. The light source device 300 causes the observation light to enter the light guide 170. The light source 310 comprises a red light source 310R, a green light source 310G, and a blue light source 310B. The red light source 310R, the green light source 310G, and the blue light source 310B eject red narrow-band light, green narrow-band light, and blue narrow-band light, respectively.

The light source 310 may generate observation light in which red narrow-band light, green narrow-band light, and blue narrow-band light are combined arbitrarily. For example, the light source 310 may generate white light by combining red narrow-band light, green narrow-band light, and blue narrow-band light. Further, the light source 310 may generate narrow-band light by arbitrarily combining two colors of red narrow-band light, green narrow-band light, and blue narrow-band light.

The light source 310 may generate narrow-band light by using any one color of red narrow-band light, green narrow-band light, and blue narrow-band light. The light source 310 may selectively switch and eject white light or narrow-band light. The narrow-band light is synonymous with special light. The light source 310 may comprise an infrared light source that ejects infrared light, an ultraviolet light source that ejects ultraviolet light, and the like.

The light source 310 may adopt an aspect comprising a white light source that ejects white light, a filter that transmits white light, and a filter that transmits narrow-band light. The light source 310 of such an aspect may selectively eject any of white light or narrow-band light by switching between the filter transmitting white light and the filter transmitting narrow-band light.

The filter transmitting narrow-band light may include a plurality of filters corresponding to different bands. The light source 310 may selectively eject a plurality of rays of narrow-band light in different bands by selectively switching the plurality of filters corresponding to the different bands.

Types, wavelength ranges, and the like according to the kinds of observation targets, observation purpose, and the like may be applied to the light source 310. As the types of the light source 310, a laser light source, a xenon light source, a light-emitting diode (LED) light source, and the like are exemplified.

The light guide connector 108 is connected to the light source device 300 so that the incident end of the light guide 170 is disposed on an optical path of light emitted from the condenser lens 340. The observation light ejected from the light source 310 reaches the incident end of the light guide 170 via the stop 330 and the condenser lens 340. The observation light is transferred to the illumination lenses 123A and 123B via the light guide 170 and is emitted to the observation range from the illumination lenses 123A and 123B.

The light source control unit 350 transmits control signals to the light source 310 and the stop 330 on the basis of the instruction signals transmitted from the processor device 200. The light source control unit 350 controls illuminance of the observation light, switching of the observation light, and on and off of the observation light ejected from the light source 310.

Configuration of Processor Device 200

The processor device 200 comprises an image input controller 202, an image processing unit 204, a communication control unit 205, a video output unit 206, and a storage unit 207. Further, the processor device 200 comprises a CPU 210, a read only memory (ROM) 211, a random access memory (RAM) 212, an operation unit 208, a sound processing unit 209, and a speaker 209A.

The image input controller 202 acquires imaging signals from the endoscope scope 100. The image processing unit 204 processes the imaging signals acquired via the image input controller 202 to generate the endoscopic image of the observation target. The term "image" includes the meaning of the image itself and image data representing the image. The image includes the concepts of both the video and the static image. The imaging signals output from the endoscope scope 100 may be understood as an aspect of the "endoscopic image".

The image processing unit 204 may execute image quality correction by applying digital signal processing such as white balance processing and shading correction processing on the input imaging signals. The image processing unit 204 may be configured using a digital signal processing circuit dedicated to image processing. Further, a part or all of the processing functions of the image processing unit 204 may be realized by the CPU 210 executing programs. The image processing unit 204 can generate one or a plurality of spectral images on the basis of the imaging signals obtained from the endoscope scope 100. Further, the image processing unit 204 may add accessory information defined by the Digital Imaging and Communications in Medicine (DICOM) standard to the endoscopic image.

The storage unit 207 stores the endoscopic image generated using the endoscope scope 100. The storage unit 207 may store various kinds of information (accessory information) attached to the endoscopic image.

The video output unit 206 transmits various display signals including the image generated using the image processing unit 204 to the monitor 400. The monitor 400 displays the image of the observation target and the like according to the display signals output from the video output unit 206.

The communication control unit 205 controls communication with devices communicatively connected via a hospital local area network (LAN), a hospital information system (HIS), and the like. The communication protocol based on the DICOM standard may be applied to the communication control unit 205.

The CPU 210 functions as an overall control unit that controls each unit in the processor device 200 and integrally controls the entire endoscope system 10. The CPU 210 functions as a memory controller that controls the ROM 211 and the RAM 212. In the ROM 211, data such as control parameters and various programs for controlling the operations of the processor device 200 are stored.

The RAM 212 is used as a temporary storage area for data in various kinds of processing and a processing area for arithmetic processing using the CPU 210. In the RAM 212, programs to be executed by the CPU 210 are stored. The RAM 212 can be used as a buffer memory in a case of acquiring the imaging signal or the endoscopic image.

The operation unit 208 accepts the user's operation and outputs instruction signals according to the user's operation. The operation unit 208 is configured using one or a plurality of combinations of, for example, a keyboard, a mouse, a joystick, a touch panel, a foot switch, and a sound input device.

The CPU 210 acquires the instruction signal (user input signal) transmitted from the operation unit 208, and executes the processing or control corresponding to the acquired user input signal.

The sound processing unit 209 generates a sound signal representing information reported as a sound. The speaker 209A converts the sound signal generated using the sound processing unit 209 into a sound. As an example of the sound output from the speaker 209A, a message, a sound guidance, a warning sound, and the like are exemplified.

The processor device 200 executes various kinds of processing on the endoscopic image generated using the endoscope scope 100 or the endoscopic image acquired via the communication control unit 205, and displays the endoscopic image and various kinds of information attached to the endoscopic image on the monitor 400. Further, the processor device 200 can store the endoscopic image and various kinds of information attached to the endoscopic image in the storage unit 207.

Further, in the processor device 200, a diagnosis support system for the endoscopic image using AI is implemented. Although the details are described below, the processor device 200 comprises a site information acquisition function of acquiring site information indicating which site in the human body is shown in the endoscopic image of the observation target, and a lesion detection function of detecting a lesion from the endoscopic image and acquiring lesion type information, and further comprises a function of determining the consistency between the site information and the lesion type information and controlling report modes of the site information and the lesion type information. The processor device 200 is an example of the "medical image processing device" in the present disclosure. The monitor 400 is an example of the "display" in the present disclosure.

Outline of Medical Image Processing Device According to First Embodiment

Figure 3:
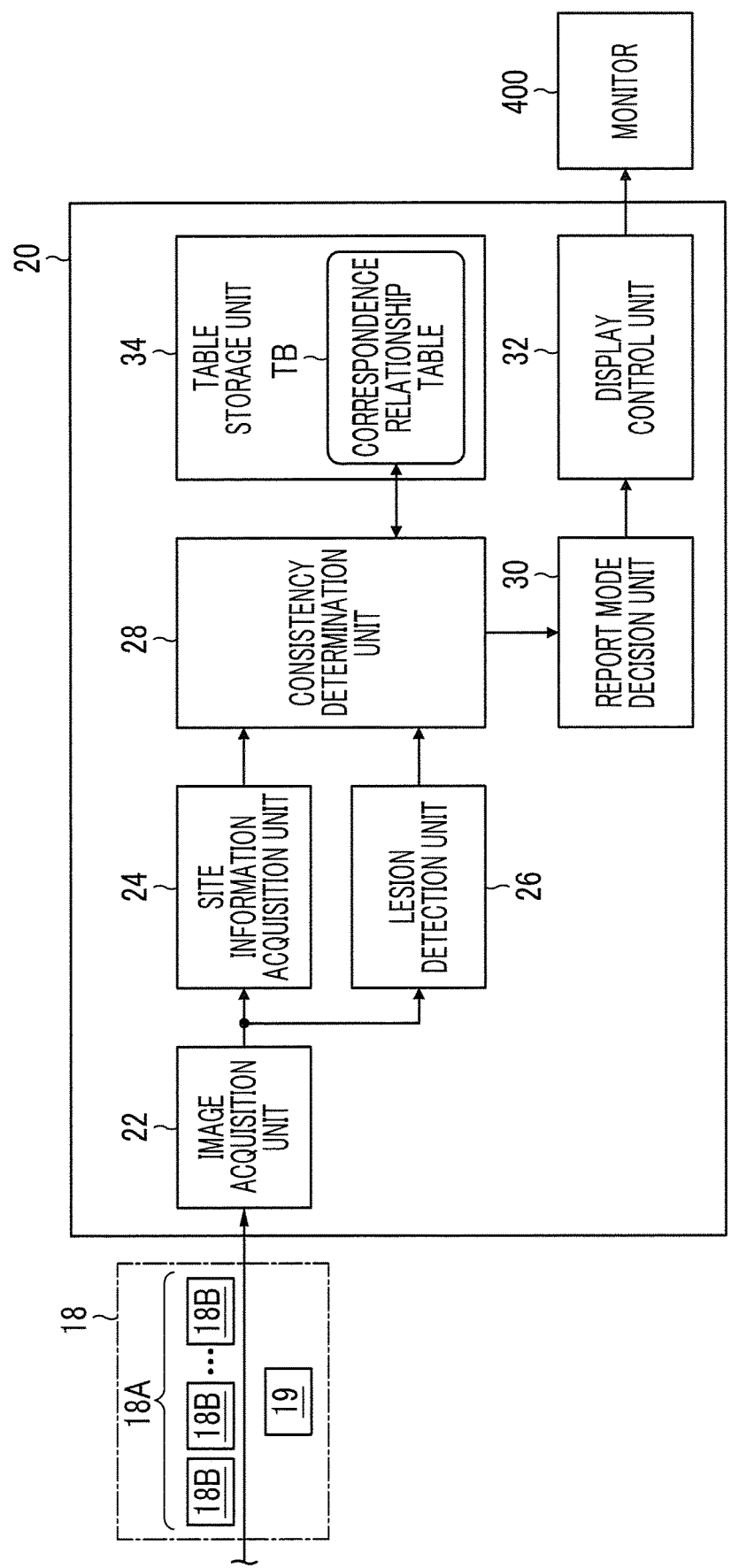
FIG. 3 is a functional block diagram illustrating functions of a medical image processing device according to a first embodiment.

FIG. 3 is a functional block diagram illustrating functions of a medical image processing device 20 according to the first embodiment of the invention. The medical image processing device 20 comprises an image acquisition unit 22, a site information acquisition unit 24, a lesion detection unit 26, a consistency determination unit 28, a report mode decision unit 30, a display control unit 32, and a table storage unit 34.

The image acquisition unit 22 acquires an endoscopic image 18 captured using the endoscope scope 100. The endoscopic image 18 may be an image represented by the imaging signal output from the endoscope scope 100, or may be an image generated by being processed by the image processing unit 204 illustrated in FIG. 2.

The image input controller 202 illustrated in FIG. 2 may function as the image acquisition unit 22. The image acquisition unit 22 may be configured to include a communication interface for importing the endoscopic image 18 from an external device via a communication line, or may be configured to include a media interface for importing the endoscopic image stored in a portable information storage medium such as a memory card. The communication control unit 205 illustrated in FIG. 2 may function as the image acquisition unit 22.

The image acquisition unit 22 may be a data input interface and/or a data input terminal which accepts an input of the endoscopic image 18 from a processing circuit inside the processor device 200 illustrated in FIG. 2. For example, the image acquisition unit 22 may be a terminal that receives an input of the endoscopic image 18 generated by the image processing unit 204 in FIG. 2. The endoscopic image 18 is an example of the "medical image" in the present disclosure.

The image acquisition unit 22 may acquire a video 18A composed of time-series frame images 18B captured by the endoscope scope 100. Further, in a case where a static image capturing instruction is input from the user during the capturing of the video 18A so that capturing of a static image 19 is executed, the image acquisition unit 22 may acquire the static image 19 captured according to the static image capturing instruction.

The site information acquisition unit 24 is a processing unit that acquires site information indicating the site of the object in the human body, which is shown in the endoscopic image 18 acquired via the image acquisition unit 22. Here, the term "site" is the human organ such as the esophagus, the stomach, or the duodenum, and the site information may be a label corresponding to the name of the organ.

As the site information acquisition unit 24, a site recognizer that acquires site information by image recognition can be used. The site recognizer performs image classification processing of recognizing an observation scene of the endoscopic image 18 and assigning a label of the site shown in the endoscopic image 18. The site recognizer is configured using a learned model such as a neural network learned by machine learning such as deep learning.

The site information acquisition unit 24 can be configured using a learned convolutional neural network (CNN) machine-learned to output a site label using the endoscopic image 18 as an input. The site information acquisition unit 24 may be understood as an AI processing unit that recognizes a site from the endoscopic image 18. The neural network applied to the site information acquisition unit 24 is an example of the "first neural network" in the present disclosure.

The site information acquisition unit 24 receives an input of the endoscopic image 18 and outputs the site information as the recognition result (inference result) and information indicating the reliability thereof. The information indicating the reliability may be a score value indicating the certainty (confidence level) of the recognized site (class), or a class belonging probability calculated by reflecting the score value. The information obtained in the site information acquisition unit 24 is sent to the consistency determination unit 28. The site information acquisition unit 24 may execute the site recognition processing on each frame image for a part or all of the plurality of frame images 18B acquired in a time-series manner.

The lesion detection unit 26 is a processing unit that detects the lesion shown in the endoscopic image acquired via the image acquisition unit 22 and generates information indicating the position of the lesion and lesion type information indicating the lesion type. Here, the information indicating the position of the lesion may be lesion region information indicating an image region of the lesion extracted from the endoscopic image, may be lesion position information indicating the position of the lesion region, or may be a combination thereof. The lesion type information may be a lesion type label corresponding to the lesion type such as squamous cell carcinoma or gastric ulcer.

As the lesion detection unit 26, a lesion detector that recognizes the position of the lesion from the endoscopic image and performs an object detection task of performing class classification of the lesion and assigning a lesion type label can be used. The lesion detector is configured using a learned model such as a neural network learned by machine learning such as deep learning.

The lesion detection unit 26 can be configured using a learned convolutional neural network machine-learned to output a lesion type label using the endoscopic image as an input. As an object detection algorithm in the lesion detection unit 26, for example, an algorithm such as Regions with CNN features (R-CNN) or Region-Based Convolutional Neural Networks (Faster R-CNN) can be used. The neural network applied to the lesion detection unit 26 is an example of the "second neural network" in the present disclosure.

The lesion detection unit 26 may be understood as an AI processing unit that performs extraction of the lesion region from the endoscopic image 18 and multi-class classification of the lesion type. The lesion detection unit 26 receives an input of the endoscopic image 18 and outputs the lesion position information and the lesion type information as the recognition result (inference result) and information indicating the reliability thereof. The information on the lesion obtained in the lesion detection unit 26 is sent to the consistency determination unit 28. The lesion detection unit 26 may execute the lesion detection processing of the site on each frame image 18B for a part or all of the plurality of frame images 18B acquired in a time-series manner.

The consistency determination unit 28 is a processing unit that determines the presence or absence of a contradiction between the site information acquired from the site information acquisition unit 24 and the lesion type information acquired from the lesion detection unit 26. The consistency determination unit 28 determines whether there is a contradiction in the relationship between the site information and the lesion type information using a correspondence relationship table TB stored in the table storage unit 34. The correspondence relationship table TB is a table in which correspondence relationships between a plurality kinds of sites and the lesion types for each site are described. Such a correspondence relationship table TB is created on the basis of the medical knowledge.

The table storage unit 34 is a storage device including a storage area where the correspondence relationship table TB is stored, and for example, is configured using a computer-readable medium as a semiconductor memory and/or a hard disk device. In the table storage unit 34, the correspondence relationship table TB used in the determination processing by the consistency determination unit 28 is stored.

Figures 4, 5:
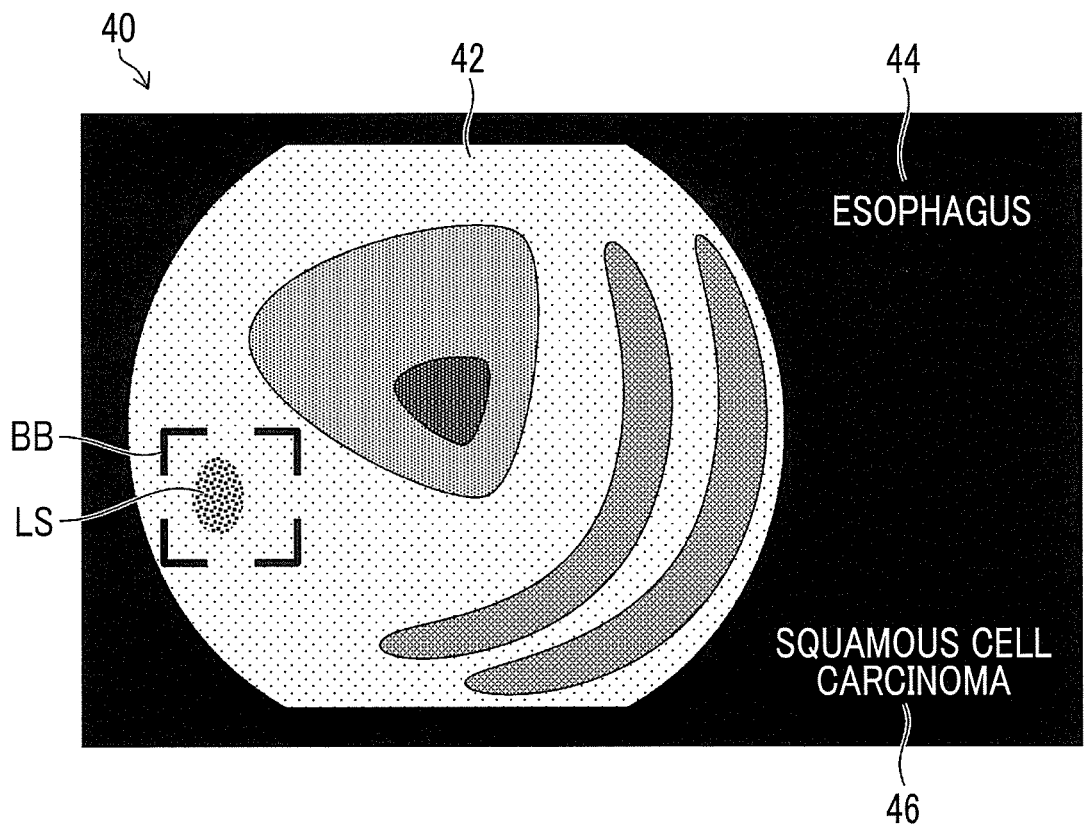
FIG. 4 is a table illustrating an example of a correspondence relationship table in which relationships of sites and lesion types are described.
FIG. 5 is an example of a display image displayed on a screen of a monitor.

FIG. 4 illustrates an example of the correspondence relationship table TB. FIG. 4 illustrates an example of table data in which information on the lesion types that may be detected in each site is tabulated for two kinds of sites of "esophagus" and "stomach" as the classification label of the site. The lesion types such as "Barrett's adenocarcinoma", "squamous cell carcinoma", "esophageal hiatus hernia", and "reflux esophagitis" associated with the "esophagus" are lesions that can be detected only in a case where the target site is the esophagus.

Further, the lesion types such as "stomach cancer", "gastric ulcer", "hyperplastic polyp", and "fundic gland polyp" associated with the "stomach" are lesions that can be detected only in a case where the target site is the stomach.

The consistency determination unit 28 illustrated in FIG. 3 creates a set of information of the site information obtained from the site information acquisition unit 24 and the lesion type information obtained from the lesion detection unit 26, and compares the set of information with the correspondence relationship table TB to determine whether there is a contradiction in the combination of the site information and the lesion type information.

In a case where the information combination of the site information obtained from the site information acquisition unit 24 and the lesion type information obtained from the lesion detection unit 26 is included in the correspondence relationship table TB, the consistency determination unit 28 determines that "there is no contradiction (matching) between the site information and the lesion type information". On the other hand, in a case where the information combination of the site information obtained from the site information acquisition unit 24 and the lesion type information obtained from the lesion detection unit 26 is not included in the correspondence relationship table TB, the consistency determination unit 28 determines that "there is a contradiction (non-matching) between the site information and the lesion type information".

The report mode decision unit 30 is a processing unit that decides the report mode of the site information and the lesion type information on the basis of the determination result of the consistency determination unit 28. The report mode decision unit 30 controls the report mode so that the combination of the contradicting information is not reported as it is. In a case where the combination of the contradicting information is generated, the report mode decision unit 30 decides not to report at least one of the site information or the lesion type information according to a predetermined rule, for example.

The display control unit 32 controls the display content of the monitor 400 according to the report mode decided by the report mode decision unit 30. That is, the display control unit 32 generates the display signal required for the display output to the monitor 400. The display signal includes a display signal for performing a report regarding the site information and the lesion type information in addition to the display signal representing the endoscopic image 18. The display signal is an example of the "report control signal" in the present disclosure. The display control unit 32 outputs the display signal to the monitor 400. The monitor 400 displays the endoscopic image 18 and the like according to the display signal. The display control unit 32 corresponds to the video output unit 206 illustrated in FIG. 2.

The CPU 210 illustrated in FIG. 2 may function as the site information acquisition unit 24, the lesion detection unit 26, and the consistency determination unit 28. The combination of the image processing unit 204 and the CPU 210 illustrated in FIG. 2 may appropriately share and realize the functions of the site information acquisition unit 24, the lesion detection unit 26, and the consistency determination unit 28.

Specific Example of Report Mode

FIG. 5 is an example of a display image displayed on a screen 40 of the monitor 400. Here, an example of the endoscopic image captured using a video flexible scope for gastroduodenoscopy is illustrated. FIG. 5 is an example of an observation image in a case of observing the esophagus. The screen 40 of the monitor 400 has an observation image display region 42, a site information report region 44, and a lesion information report region 46.

The observation image display region 42 is a region in which the endoscopic image as the observation image is displayed. In the observation image display region 42, the video of the endoscopic image captured by the endoscope scope 100 during the endoscope examination is displayed in real time. In FIG. 5, an example of a case where a lesion LS is detected from the endoscopic image is illustrated. In a case where the lesion LS is detected, in the observation image display region 42, a bounding box BB surrounding the region of the lesion LS in the endoscopic image is displayed to overlap the endoscopic image. The bounding box BB is an example of the report mode of emphasizing the position of the lesion LS. The display of the bounding box BB may be a combination of L-shaped broken lines indicating the four corners of a quadrangle as illustrated in FIG. 5, or may be a rectangular frame border.

In the screen 40, the site information report region 44 and the lesion information report region 46 are provided beside the observation image display region 42. The site information report region 44 is a display region for reporting the site information. In the site information report region 44, the site information as the recognition result by the site information acquisition unit 24 is displayed as character information. The lesion information report region 46 is a display region for reporting the lesion type information. In the lesion information report region 46, the lesion type information of the lesion LS detected by the lesion detection unit 26 is displayed as the character information.

In a case where the correspondence relationship between the site where the lesion LS is present and the lesion type is consistent (in a case where there is no contradiction), as illustrated in FIG. 5, both the site information and the lesion type information are displayed beside the observation image. Here, an example in which the site recognized by the medical image processing device 20 is the "esophagus" and the detected lesion is the "squamous cell carcinoma" is illustrated. The combination of the "esophagus" and the "squamous cell carcinoma" is described in the correspondence relationship table TB (FIG. 4), and there is no contradiction in the combination.

In FIG. 5, the site information is displayed on the upper right side of the observation image display region 42 and the lesion type information is displayed on the lower right side of the observation image display region 42, but the position of the information to be displayed is not limited to the example of FIG. 5. It is preferable that the site information and the lesion type information are reported at positions that do not overlap the observation image.

Description of Problem Expected in Case where Recognition Miss is Generated

Figure 6:
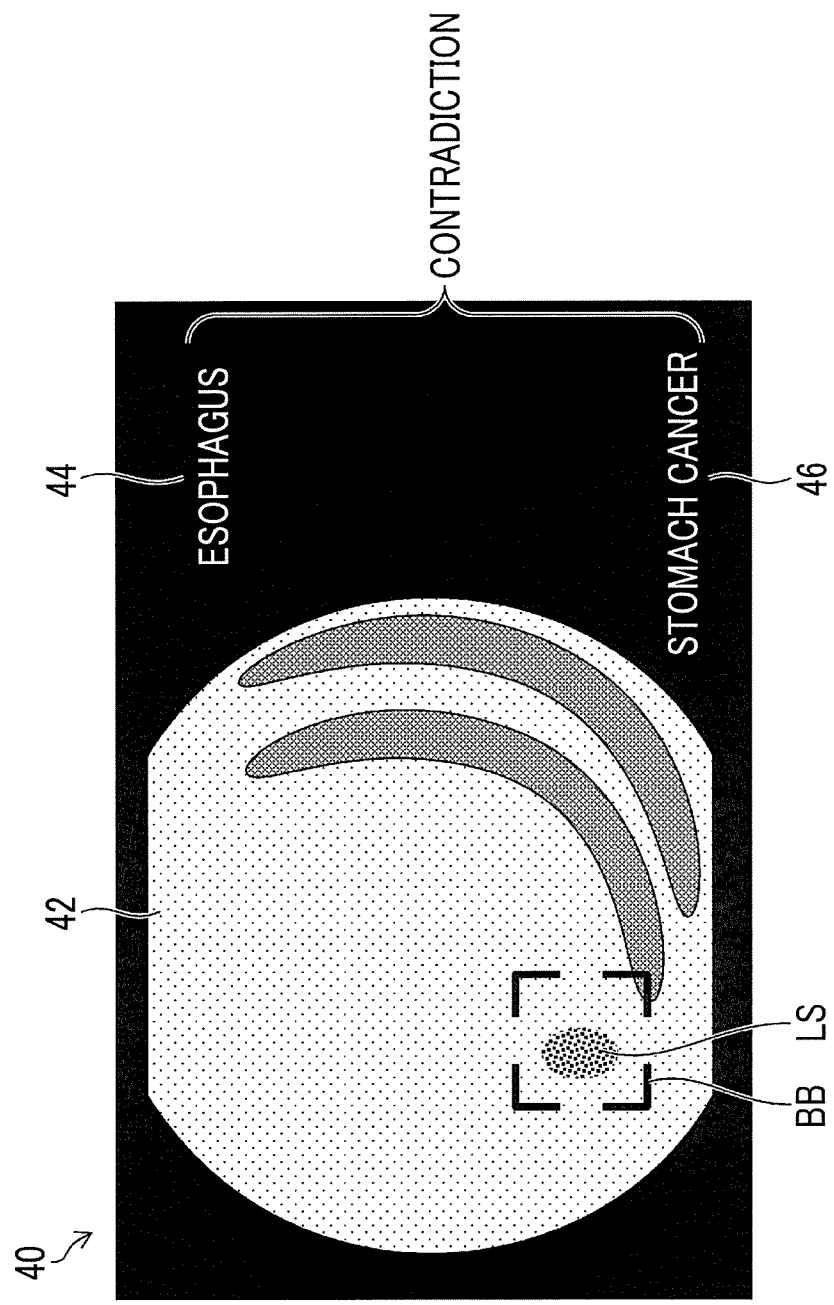
FIG. 6 is an example of a display image in a case where an inappropriate report expected in an endoscope system of a comparative example is performed.

FIG. 6 is an example of a display image in a case where an inappropriate report expected in an endoscope system of a comparative example is performed. The endoscope system of the comparative example is configured not to comprise the consistency determination unit 28, the report mode decision unit 30, and the table storage unit 34 described in FIG. 3, and is configured to independently display the recognition result of the site information acquisition unit 24 and the detection result of the lesion detection unit 26 as they are on the monitor 400.

In such an endoscope system according to the comparative example, for example, in a case where the site information acquisition unit 24 erroneously recognizes the site and outputs an incorrect recognition result, there is a contradiction between the reported site information and the reported lesion type information as illustrated in FIG. 6. FIG. 6 is an example of an observation image in a case of observing the stomach. That is, the result of the site recognition is the "esophagus" but the lesion detection unit 26 may recognize the lesion as the "stomach cancer".

Example of Report Mode by Medical Image Processing Device 20 According to Embodiment In order to avoid the inappropriate report including the contradicting information as described in FIG. 6, in a case where there is a contradiction in the information as described above, the medical image processing device 20 according to the embodiment performs the following operations, for example.

Example 1

In a case where there is a contradiction between the site information and the lesion type information, the report mode decision unit 30 compares the reliability of the site information with the reliability of the lesion type information, and decides not to report the information with the lower reliability and decide to report only the information with higher reliability.

Example 2

In a case where there is a contradiction between the site information and the lesion type information, the report mode decision unit 30 decides not to report the site information and decides to report the lesion type information.

Example 3

In a case where there is a contradiction between the site information and the lesion type information, the report mode decision unit 30 compares each of the reliability of the site information and the reliability of the lesion type information with the reference value, and decides not to report both the site information and the lesion type information in a case where both the reliabilities are lower than the reference value.

Example 4

In a case where there is a contradiction between the site information and the lesion type information, the report mode decision unit 30 decides to report that there is a contradiction. The report based on the algorithm in Example 4 can be performed in combination with any one mode of Examples 1 to 3.

Figure 7:
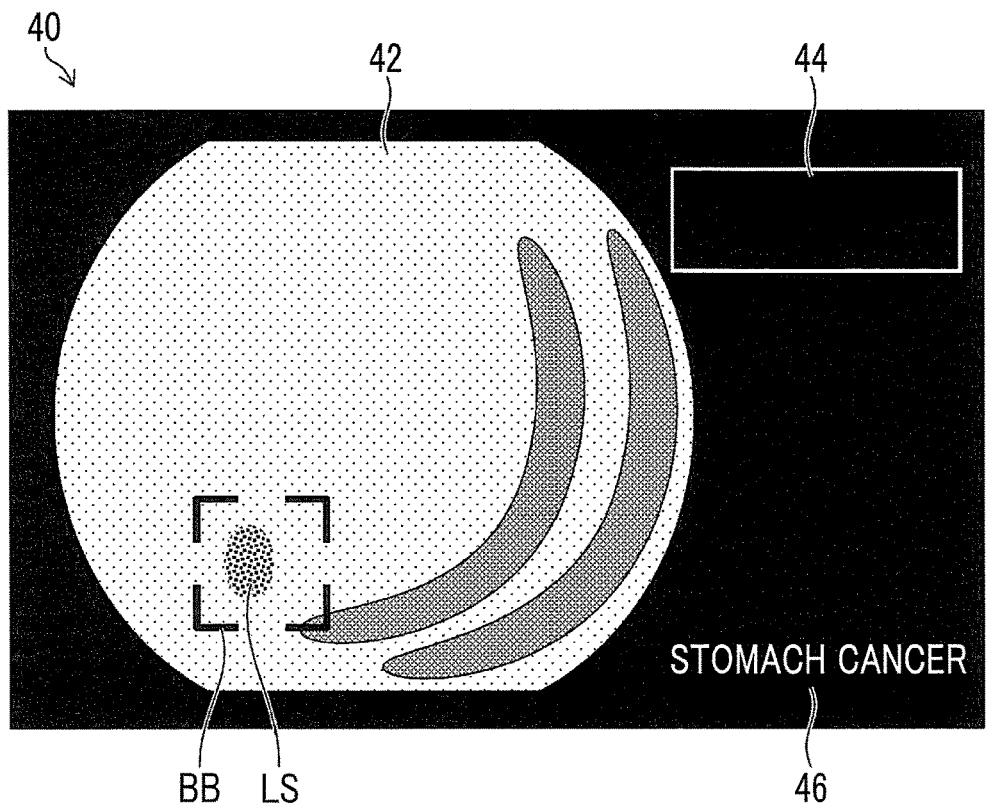
FIG. 7 is an example of a display image in a case where site information is not reported and lesion type information is reported by the medical image processing device according to the embodiment.

FIG. 7 is an example of a display image in a case where the site information is not reported and the lesion type information is reported by the medical image processing device according to the embodiment. In FIG. 7, in order to clearly illustrate that the site information is not reported, the site information report region 44 is indicated by a rectangular box frame to illustrate that the site information report region 44 is blank, but the display of the box frame is not necessary on the actual screen 40. The same applies to FIGS. 8 and 9.

Figure 8:
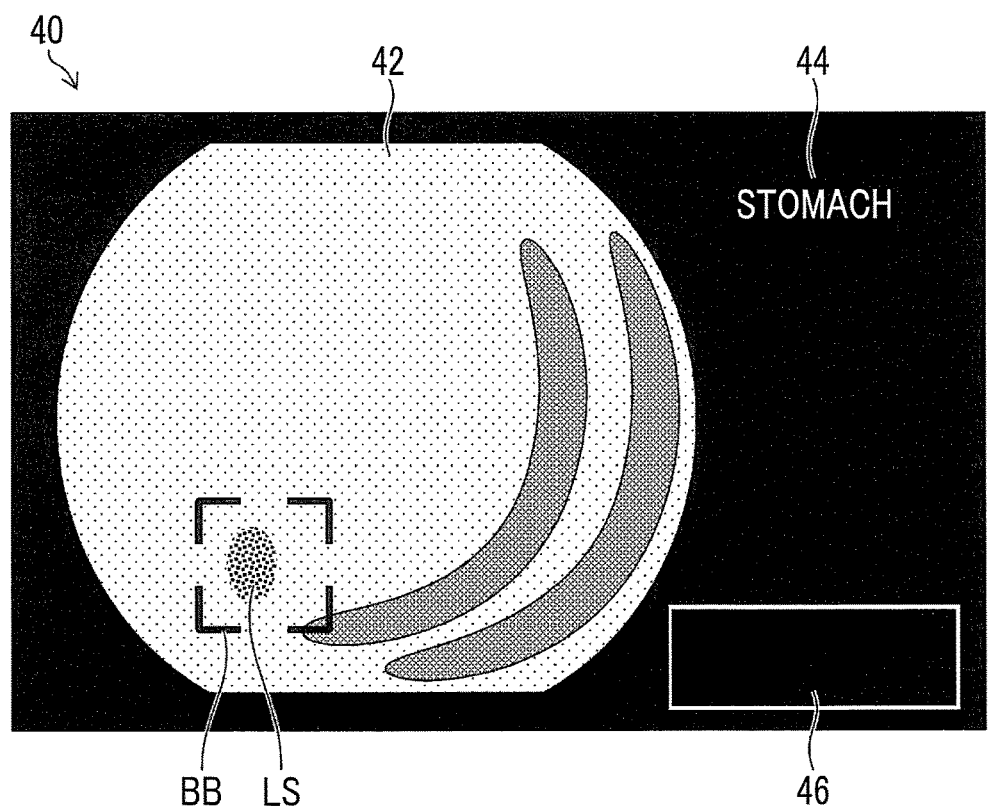
FIG. 8 is an example of a display image in a case where lesion type information is not reported and site information is reported by the medical image processing device according to the embodiment.

FIG. 8 is an example of a display image in a case where the lesion type information is not reported and the site information is reported by the medical image processing device 20 according to the embodiment.

Figure 9:
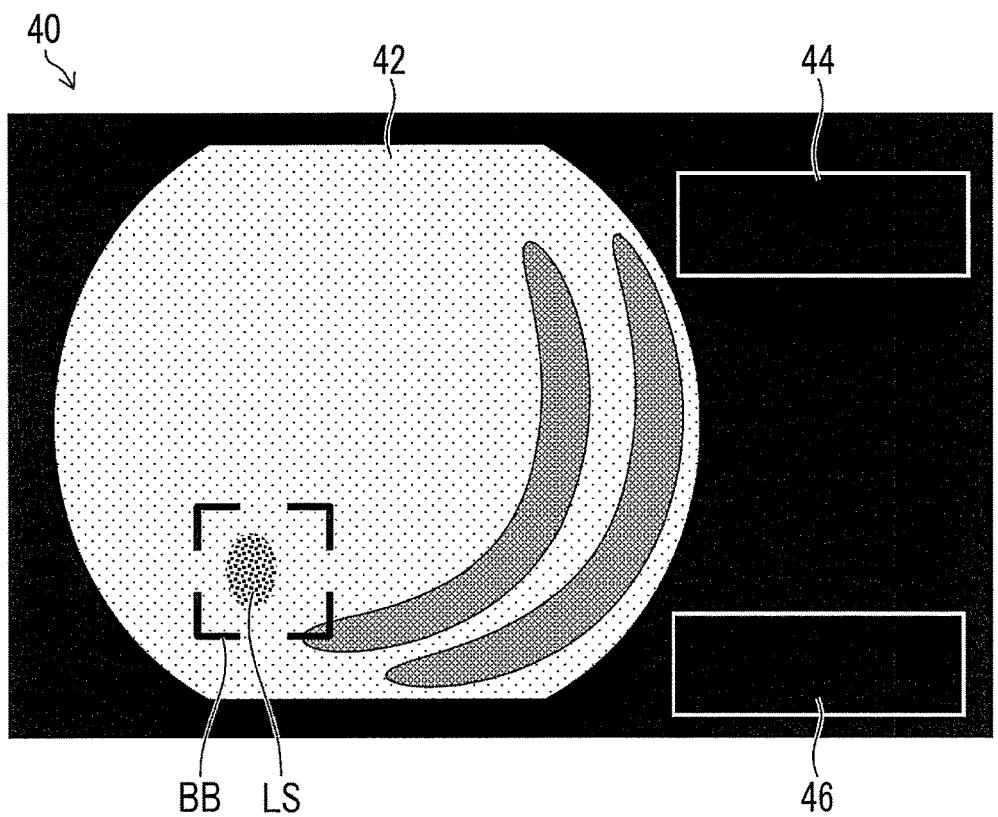
FIG. 9 is an example of a display image in a case where both site information and lesion type information are not reported by the medical image processing device according to the embodiment.

FIG. 9 is an example of a display image in a case where both the site information and the lesion type information are not reported by the medical image processing device 20 according to the embodiment.

Figure 10:
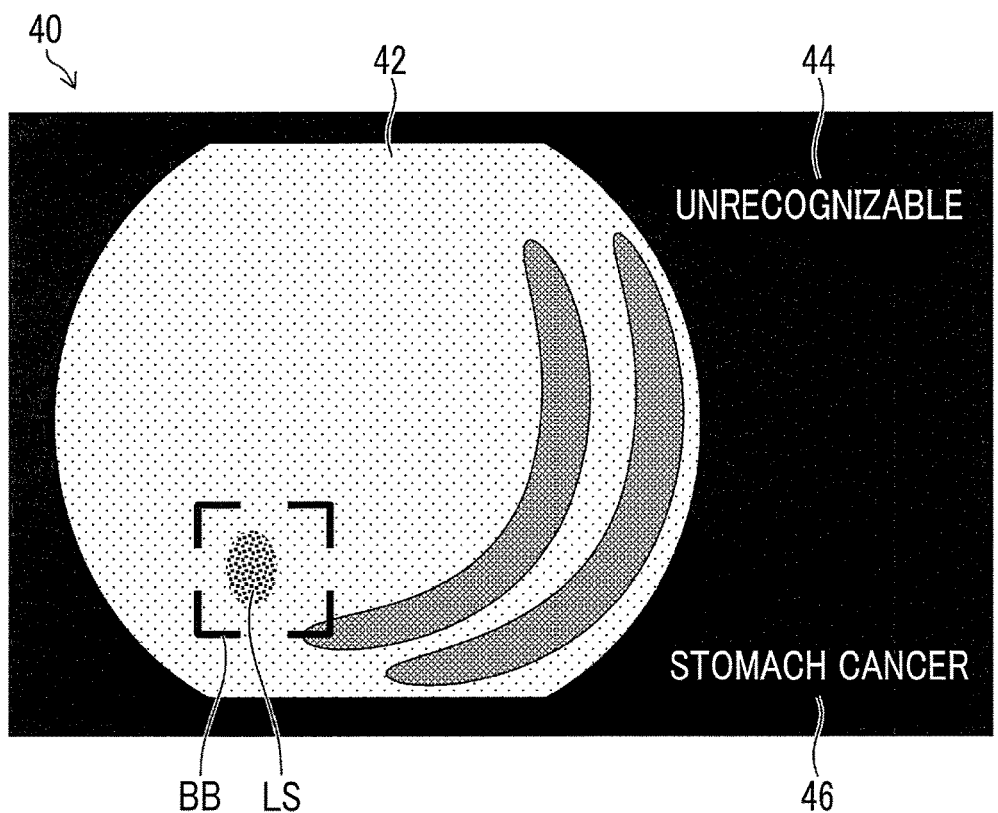
FIG. 10 is an example of a display image in a case of reporting that there is a contradiction between a result of site recognition and a result of lesion detection by the medical image processing device according to the embodiment.

FIG. 10 is an example of a display image in a case of reporting that there is a contradiction between the result of the site recognition and the result of the lesion detection by the medical image processing device 20 according to the embodiment. In the example illustrated in FIG. 10, the site information with the lower reliability of the site information and the lesion type information is not reported, and instead of reporting the site information, character information of "unrecognizable" is displayed in the site information report region 44.

With the medical image processing device 20 according to the embodiment, the report of contradicting information is avoided, and useful diagnosis support for the user is possible.

The medical image processing device 20 is not limited to a form of being mounted on the processor device 200, and can be applied to an information processing apparatus different from the processor device 200. For example, the processing functions of the medical image processing device 20 may be implemented in an image processing server or the like connected to a hospital network.

Example of Hardware Configuration of Medical Image Processing Device 20

Figure 11:
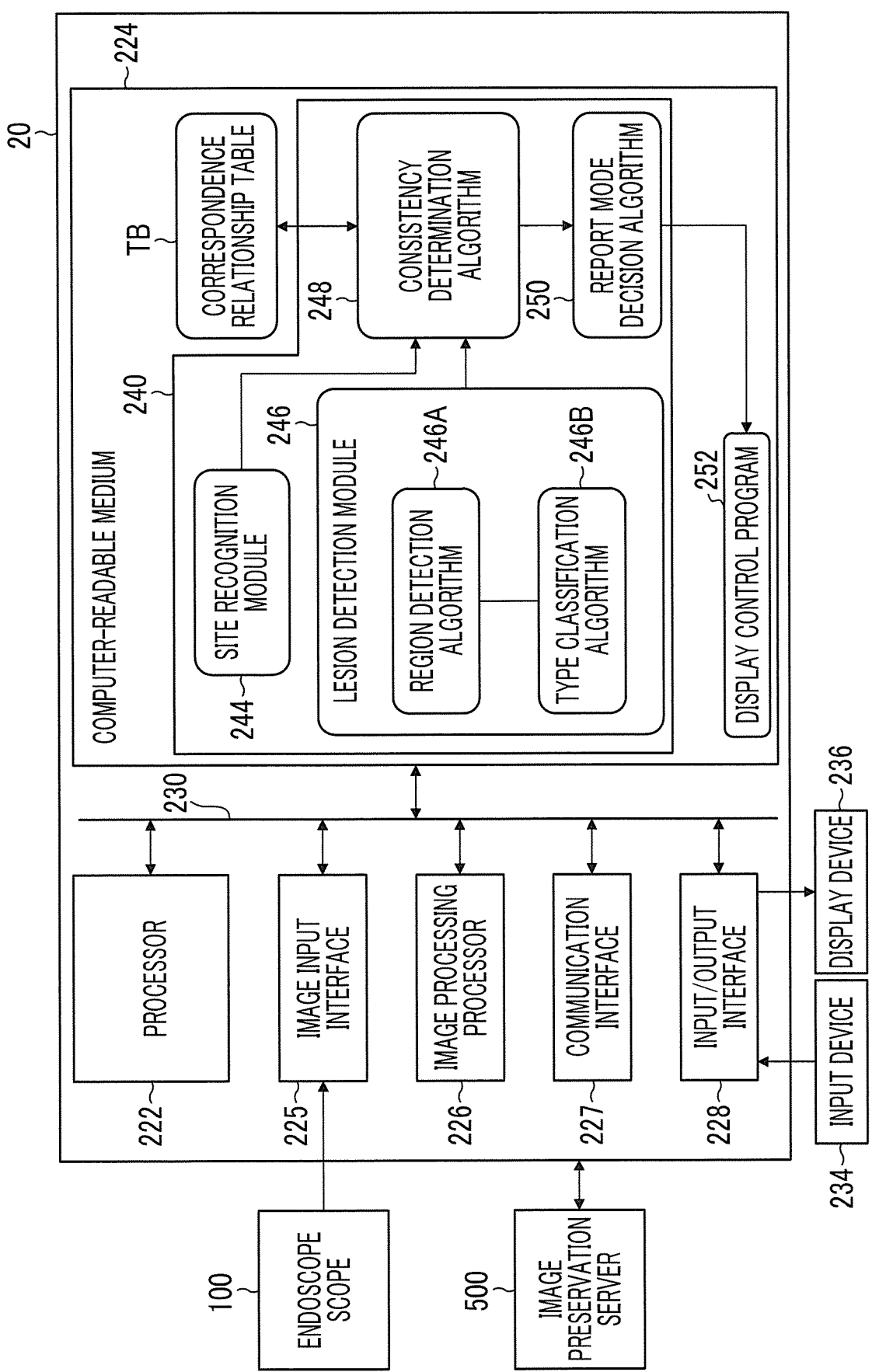
FIG. 11 is a block diagram illustrating an example of a hardware configuration of the medical image processing device according to the first embodiment.

FIG. 11 is a block diagram illustrating an example of a hardware configuration of the medical image processing device 20. The medical image processing device 20 can be realized by a computer system configured using one or a plurality of computers. That is, the medical image processing device 20 is realized by installing a program in the computer.

The medical image processing device 20 comprises a processor 222, a tangible non-transitory computer-readable medium 224, an image input interface 225, an image processing processor 226, a communication interface 227, an input/output interface 228, and a bus 230.

The processor 222 includes a CPU. The processor 222 may include a graphics processing unit (GPU). The processor 222 is connected to the computer-readable medium 224, the image input interface 225, the image processing processor 226, the communication interface 227, and the input/output interface 228 via the bus 230. The medical image processing device 20 may further comprise an input device 234 and a display device 236. The input device 234 and the display device 236 are connected to the bus 230 via the input/output interface 228.

The computer-readable medium 224 includes a memory as a main storage device and a storage as an auxiliary storage device. For example, the computer-readable medium 224 may be a semiconductor memory, a hard disk drive (HDD) device, or a solid state drive (SSD) device or a combination of a plurality thereof.

The image input interface 225 may function as the image acquisition unit 22 illustrated in FIG. 3. The medical image processing device 20 is connected to the endoscope scope 100 via the image input interface 225.

The image processing processor 226 is a processor dedicated to image processing corresponding to the image processing unit 204 illustrated in FIG. 2.

The communication interface 227 corresponds to the communication control unit 205 illustrated in FIG. 2. The medical image processing device 20 is connected to a communication line (not illustrated) via the communication interface 227. The communication line may be a local area network (LAN) constructed in a hospital. A communication network in a hospital is called a hospital network. The hospital network may be further connected to a wide area network such as the Internet via a router. An image preservation server 500 such as a picture archiving and communication systems (PACS) server is connected to the hospital network.

The PACS server is a computer that preserves and manages various kinds of data including the medical image captured using various modalities, and comprises a large-capacity external storage device and software for database management. The PACS server performs communication with other devices via the hospital network, and transmits and receives various kinds of data including the image data. The PACS server may be a DICOM server operating on the basis of the DICOM protocol.

The medical image processing device 20 may acquire the endoscopic image from the image preservation server 500 connected via the communication interface 227.

In the computer-readable medium 224, a diagnosis support program 240, the correspondence relationship table TB, and a display control program 252 are stored. The diagnosis support program 240 includes a site recognition module 244, a lesion detection module 246, a consistency determination algorithm 248, and a report mode decision algorithm 250. The site recognition module 244 is a program module including a command for causing the processor 222 to execute processing as the site information acquisition unit 24 described in FIG. 3.

The lesion detection module 246 is a program module including a command for causing the processor 222 to execute processing as the lesion detection unit 26 described in FIG. 3. The lesion detection module 246 includes a region detection algorithm 246A for detecting a region of a lesion from the endoscopic image 18, and a type classification algorithm 246B for performing a class classification task of classifying the lesion detected from the endoscopic image 18 and assigning a lesion type label. Here, the "algorithm" is a constituent of a program including a command for causing the execution of the processor 222.

Each of the region detection algorithm 246A and the type classification algorithm 246B may be configured as a program module, or the region detection algorithm 246A and the type classification algorithm 246B may be implemented as a program module integrally configured.

The consistency determination algorithm 248 includes a command for causing the processor 222 to execute processing as the consistency determination unit 28 described in FIG. 3. The report mode decision algorithm 250 includes a command for causing the processor 222 to execute processing as the report mode decision unit 30 described in FIG. 3.

The display control program 252 is a program including a command for causing the processor 222 to execute processing as the display control unit 32 described in FIG. 3. A part or all of the display control program 252 may be incorporated in the diagnosis support program 240.

Further, in the computer-readable medium 224, an image processing program (not illustrated) including a command for causing the processor 222 to execute a part or all of processing as the image processing unit 204 described in FIG. 3 may be stored.

The input device 234 corresponds to the operation unit 208 illustrated in FIG. 2. The input device 234 may be, for example, a keyboard, a mouse, a touch panel, a foot switch, or a sound input device, or an appropriate combination thereof. The user can input various instructions by operating the input device 234.

The display device 236 may be, for example, a liquid crystal display, an organic electro-luminescence (OEL) display, or a projector, or an appropriate combination thereof. The display device 236 may display an image to be processed and various kinds of information such as various kinds of setting information required for processing, in addition to the recognition result. The display device 236 corresponds to the monitor 400 illustrated in FIG. 2. The display device 236 is an example of the "display" in the present disclosure.

Figure 12:
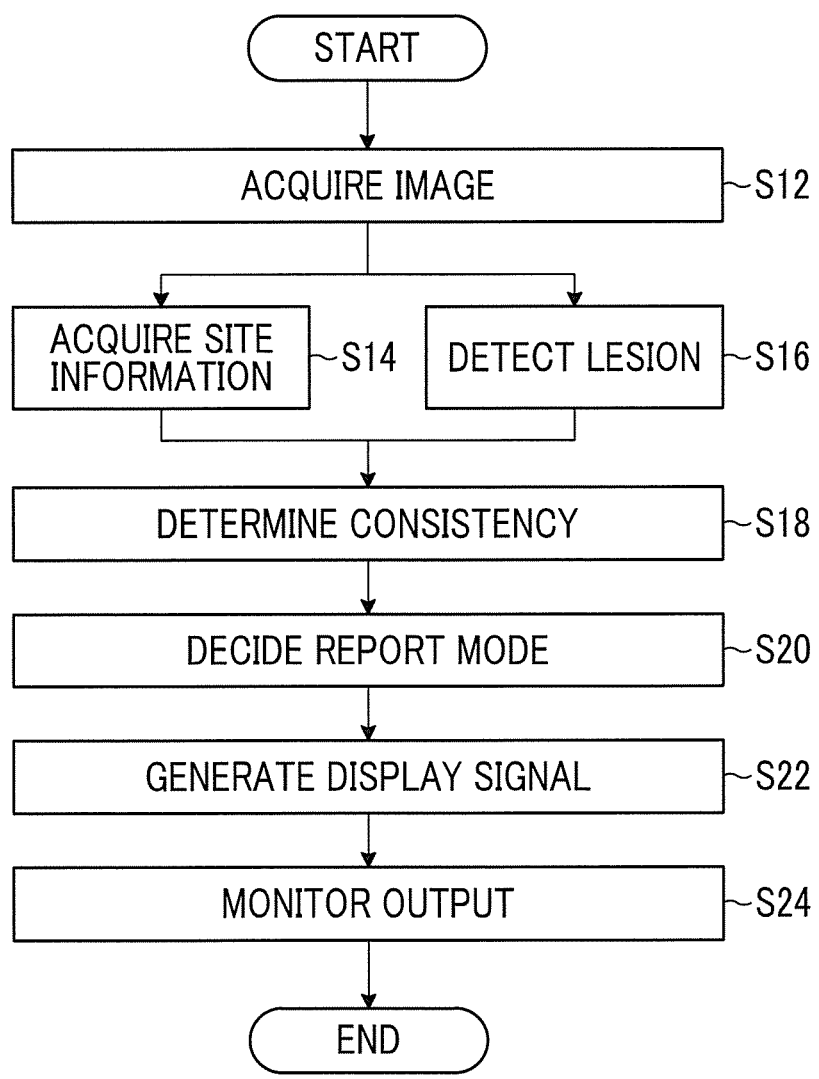
FIG. 12 is a flowchart illustrating an operation of the medical image processing device according to the first embodiment.

FIG. 12 is a flowchart illustrating the operation of the medical image processing device 20 according to the first embodiment. Each step of the flowchart of FIG. 12 is executed by the processor 222 executing the program.

In an image acquisition step of Step S12, the processor 222 acquires the endoscopic image.

In a site information acquisition step of Step S14, the processor 222 acquires the site information by recognizing the site of the observation target.

In a lesion detection step of Step S16, the processor 222 performs processing of detecting the lesion from the endoscopic image, and acquires the lesion type information in a case where the lesion is detected. The processor 222 may execute the processing of Step S14 and the processing of Step S16 in parallel and independently.

In a consistency determination step of Step S18, the processor 222 determines the presence or absence of a contradiction between the site information obtained in Step S14 and the lesion type information obtained in Step S16.

In a report mode decision step of Step S20, the processor 222 decides the report mode of the site information and the lesion type information according to the determination result of Step S18. The algorithm for deciding the report mode may be any one or a combination of a plurality of Example 1 to Example 4 described above.

In a display signal generation step of Step S22, the processor 222 generates the display signal for realizing the report of the report mode decided in Step S20.

In a monitor output step of Step S24, the processor 222 transmits the display signal generated in Step S22 to the monitor 400. As a result, on the screen 40 of the monitor 400, the report of the site information and the lesion type information is performed by an appropriate report mode.

The operation method of the medical image processing device 20 illustrated in the flowchart of FIG. 12 may be understood as the diagnosis support method that is performed by the medical image processing device 20, or may be understood as the image processing method that is performed by the medical image processing device 20.

Second Embodiment

Figure 13:
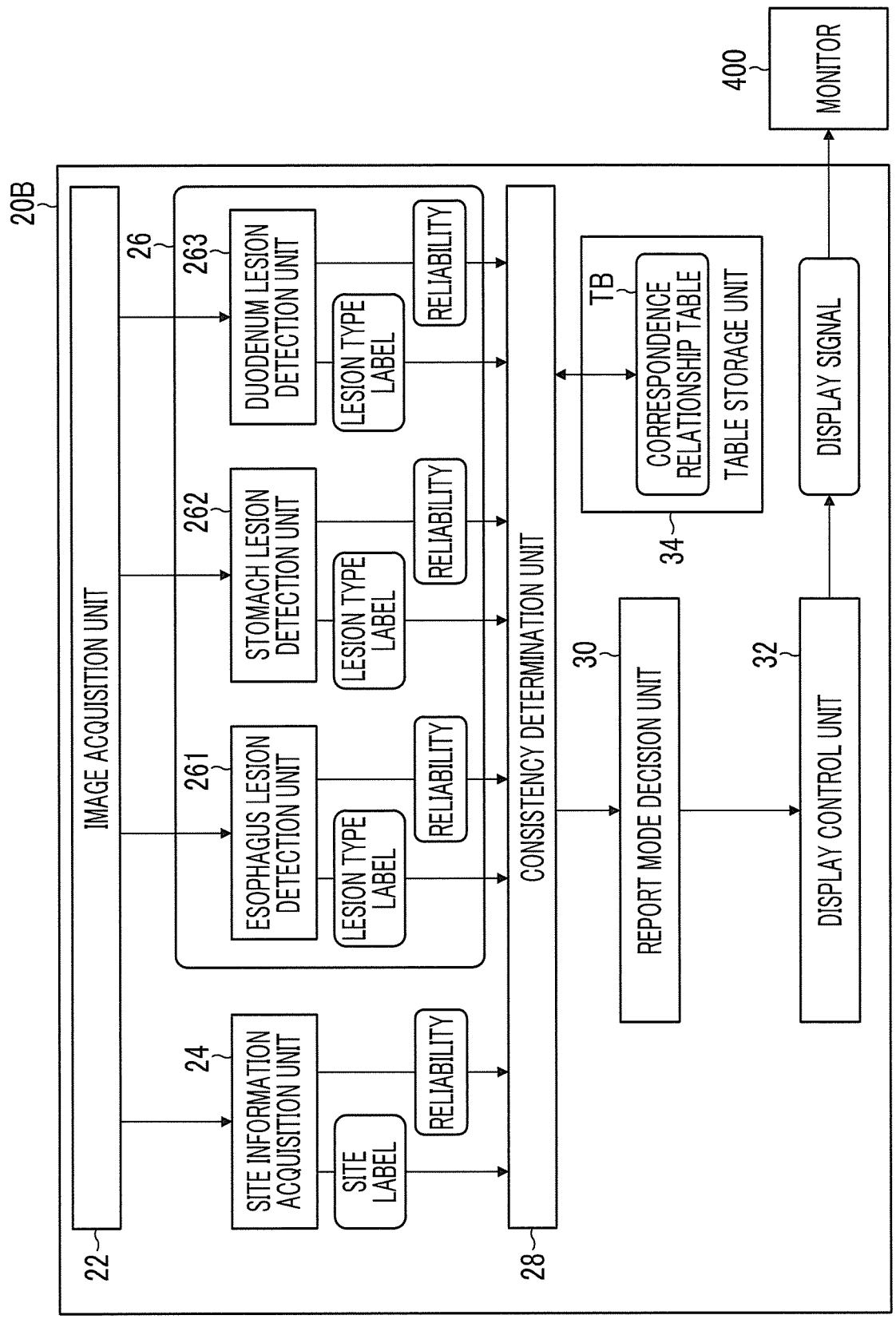
FIG. 13 is a functional block diagram illustrating a main configuration of a medical image processing device according to a second embodiment.

FIG. 13 is a functional block diagram illustrating a main configuration of a medical image processing device 20B according to a second embodiment. In FIG. 13, the same or similar elements to the configuration illustrated in FIGS. 1 to 3 and 11 are given the same reference numerals, and descriptions thereof will be omitted. The differences from the first embodiment will be described.

The medical image processing device 20B illustrated in FIG. 13 is an example in which a plurality of lesion detection units for sites as the observation targets are provided as the lesion detection unit 26. Here, assuming application to the endoscope examination of the upper digestive organ, the lesion detection unit 26 comprises an esophagus lesion detection unit 261, a stomach lesion detection unit 262, and a duodenum lesion detection unit 263. Each lesion detection unit may be a lesion detector using a learned neural network learned to detect a lesion in each site.

The esophagus lesion detection unit 261, the stomach lesion detection unit 262, and the duodenum lesion detection unit 263 execute the lesion detection processing in parallel (independently), and output the detection result.

The consistency determination unit 28 determines the consistency between the site information indicated by the site label obtained from the site information acquisition unit 24 and the lesion type information indicated by the lesion type label as the detection result obtained from each of the esophagus lesion detection unit 261, the stomach lesion detection unit 262, and the duodenum lesion detection unit 263.

The report mode decision unit 30 decides the report mode regarding the site information and the lesion type information on the basis of the determination result of the consistency determination unit 28.

Figure 14:
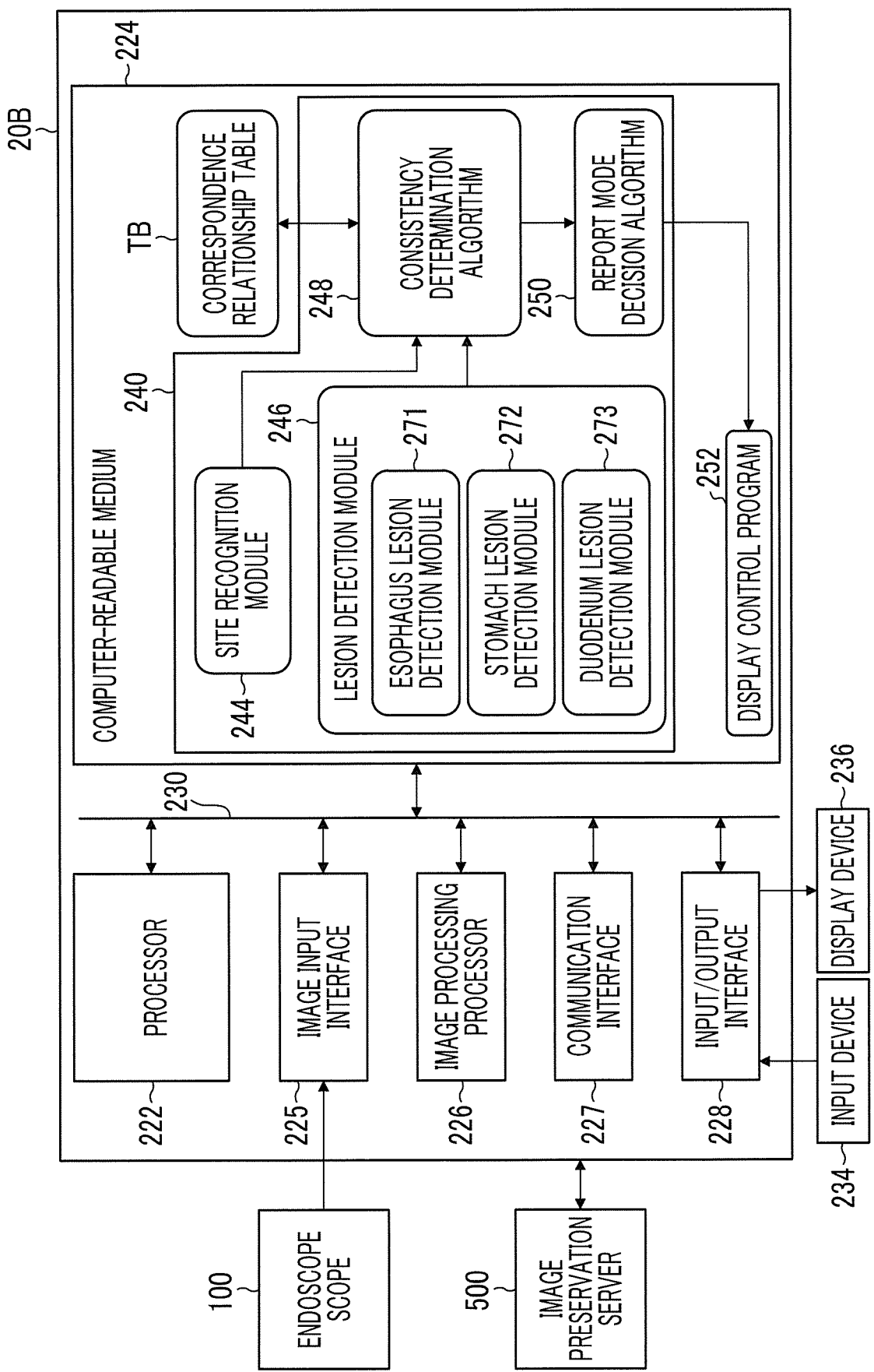
FIG. 14 is a block diagram illustrating an example of a hardware configuration of the medical image processing device according to the second embodiment.

FIG. 14 is a block diagram illustrating an example of a hardware configuration of the medical image processing device 20B according to the second embodiment. In FIG. 14, the same or similar elements to the configuration illustrated in FIG. 11 are given the same reference numerals, and descriptions thereof will be omitted.

The medical image processing device 20B illustrated in FIG. 14 is configured such that the lesion detection module 246 includes a plurality of lesion detection modules prepared for the sites. The lesion detection module 246 in FIG. 14 includes an esophagus lesion detection module 271, a stomach lesion detection module 272, and a duodenum lesion detection module 273. Each of the plurality of lesion detection modules prepared for the sites is configured to include a region detection algorithm for detecting a region of a lesion from the endoscopic image in the target site, and a type classification algorithm for classifying the lesion and assigning a lesion type label.

In FIGS. 13 and 14, an example of comprising the lesion detection unit (lesion detection module) for each site for the respective sites of the esophagus, the stomach, and the duodenum has been described, but the types of sites and the combination thereof are not limited to this example. As other sites where the endoscope examination is performed, there are various sites such as large intestine, small intestine, rectum, pancreatic duct, biliary tract, chest cavity, bronchus, ear, nose, throat, and brain.

Third Embodiment

Figure 15:
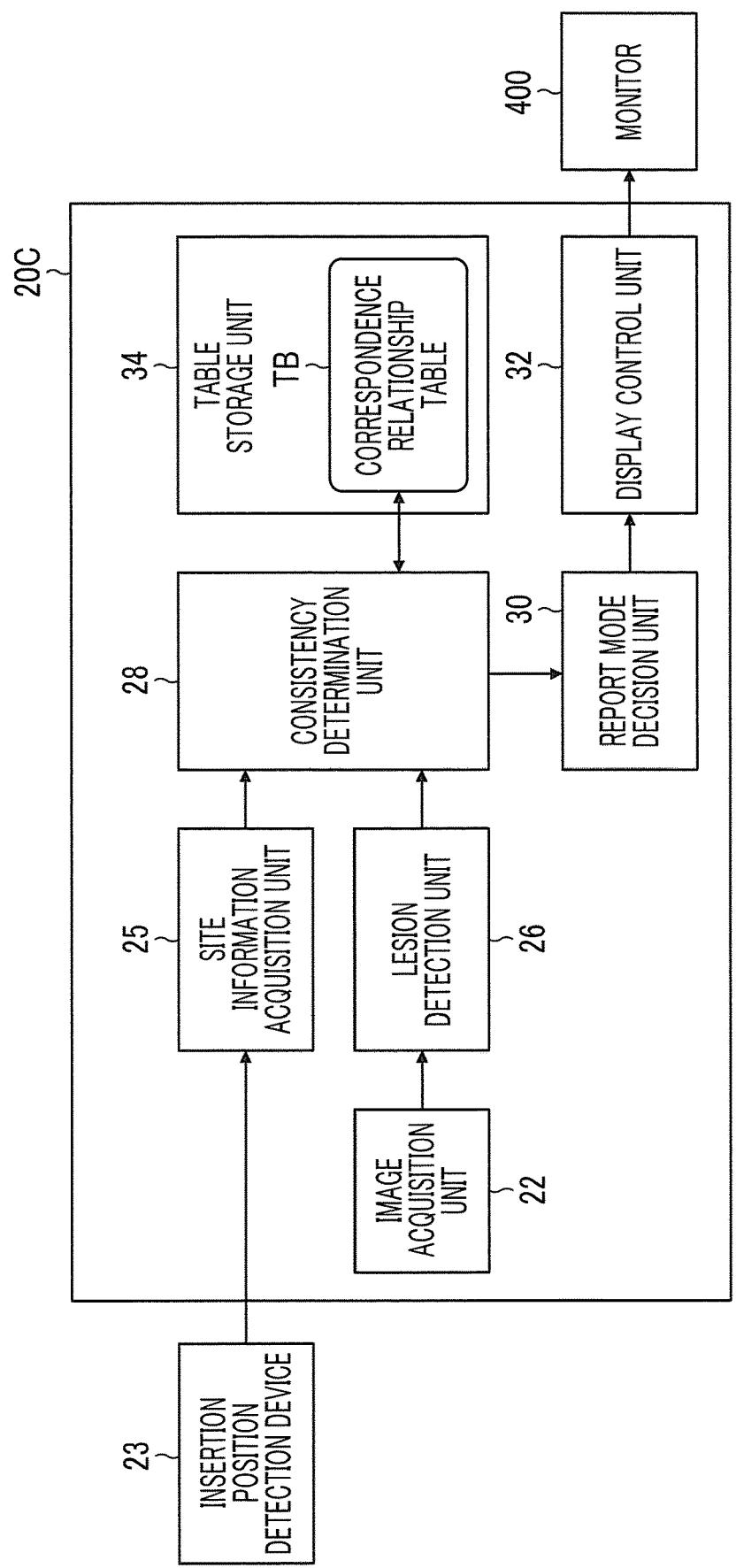
FIG. 15 is a functional block diagram illustrating functions of a medical image processing device according to a third embodiment.

FIG. 15 is a functional block diagram illustrating functions of a medical image processing device 20C according to a third embodiment. In FIG. 15, the same or similar elements to the configuration illustrated in FIG. 3 are given the same reference numerals, and descriptions thereof will be omitted.

In the first embodiment and the second embodiment, an example of acquiring the site information on the basis of the image recognition of the endoscopic image 18 has been described, but the method of acquiring the site information is not limited to that by the image recognition.

The medical image processing device 20C illustrated in FIG. 15 acquires information indicating the insertion position of the endoscope scope 100 in the body using an insertion position detection device 23, and acquires the site information from the insertion position information. The medical image processing device 20C comprises a site information acquisition unit 25 that acquires the site information on the basis of the insertion position information obtained from the insertion position detection device 23.

The insertion position detection device 23 may be a position detection sensor built in the endoscope scope 100, or may be an endoscope position detecting unit (UPD) or the like. The endoscope position detecting unit is a system that can grasp the insertion shape of the endoscope probe inside the examinee by receiving the magnetic field generated by the coil built in the endoscope probe using the endoscope position detecting unit. By using the endoscope position detecting unit, it is possible to grasp the insertion position of the endoscope probe in the body, that is, the location that is being observed. It is possible to estimate the site of the observation target by using the information on the insertion position of the endoscope probe.

The site information acquisition unit 25 may be configured to acquire the site information using a table or the like that defines the correspondence relationship between the insertion position information and the site information. Other configurations may be the same as to those of the first embodiment and the second embodiment.

Regarding Hardware Configuration of Each Processing Unit and Control Unit

The hardware structures of the processing units executing various kinds of processing, such as the image processing unit 204, the communication control unit 205, and the light source control unit 350 described in FIG. 2, the image acquisition unit 22, the site information acquisition unit 24, the lesion detection unit 26, the consistency determination unit 28, the report mode decision unit 30, and the display control unit 32 described in FIG. 3, the esophagus lesion detection unit 261, the stomach lesion detection unit 262, and the duodenum lesion detection unit 263 described in FIG. 13, and the site information acquisition unit 25 described in FIG. 15 are the following various processors.

The various processors include a central processing unit (CPU) as a general-purpose processor executing a program and functioning as various processing units, a programmable logic device (PLD) as a processor of which the circuit configuration can be changed after manufacturing such as a field programmable gate array (FPGA), and a dedicated electrical circuit as a processor having a circuit configuration designed exclusively for executing specific processing such as an application specific integrated circuit (ASIC).

One processing unit may be configured by one processor among these various processors, or may be configured by two or more same or different kinds of processors. For example, one processing unit may be configured by a plurality of FPGAs, or a combination of a CPU and a FPGA. In addition, a plurality of processing units may be configured by one processor. As an example where a plurality of processing units are configured by one processor, first, there is a form where one processor is configured by a combination of one or more CPUs and software as typified by a computer, such as a client or a server, and this processor functions as a plurality of processing units. Second, there is a form where a processor fulfilling the functions of the entire system including a plurality of processing units by one integrated circuit (IC) chip as typified by a system on chip (SoC) or the like is used. In this manner, various processing units are configured by using one or more of the above-described various processors as hardware structures.

Furthermore, the hardware structures of these various processors are more specifically electrical circuitry where circuit elements, such as semiconductor elements, are combined.

Regarding Observation Light of Endoscope System

As the observation light, light in various wavelength ranges is selected according to the observation purpose, such as white light or light in one or a plurality of specific wavelength ranges, or a combination thereof. The white light is light in a white-light wavelength range or light in a plurality of wavelength ranges. The "specific wavelength range" is a range narrower than the white-light wavelength range. Specific examples regarding the specific wavelength range are described below.

First Example

A first example of the specific wavelength range is a blue-light wavelength range or a green-light wavelength range of a visible-light wavelength range, for example. The wavelength range of the first example includes a wavelength range of 390 nm to 450 nm or a wavelength range of 530 nm to 550 nm, and light of the first example has a peak wavelength in a wavelength range of 390 nm to 450 nm or a wavelength range of 530 nm to 550 nm.

Second Example

A second example of the specific wavelength range is a red-light wavelength range of a visible-light wavelength range, for example. The wavelength range of the second example includes a wavelength range of 585 nm to 615 nm or a wavelength range of 610 nm to 730 nm, and light of the second example has a peak wavelength in a wavelength range of 585 nm to 615 nm or a wavelength range of 610 nm to 730 nm.

Third Example

A third example of the specific wavelength range includes a wavelength range where a light absorption coefficient in oxyhemoglobin is different from that in reduced hemoglobin, and light of the third example has a peak wavelength in a wavelength range where a light absorption coefficient in oxyhemoglobin is different from that in reduced hemoglobin. The wavelength range of the third example includes a wavelength range of 400±10 nm, a wavelength range of 440±10 nm, a wavelength range of 470±10 nm, or a wavelength range of 600 nm to 750 nm, and light of the third example has a peak wavelength in a wavelength range of 400±10 nm, 440±10 nm, 470±10 nm, or 600 nm to 750 nm.

Fourth Example

A fourth example of the specific wavelength range is a wavelength range of excitation light which is used for observation (fluorescence observation) of fluorescence emitted by fluorescent materials in a living body and excites the fluorescent materials, which is 390 nm to 470 nm, for example.

Fifth Example

A fifth example of the specific wavelength range is an infrared wavelength range. The wavelength range of the fifth example includes a wavelength range of 790 nm to 820 nm or a wavelength range of 905 nm to 970 nm, and light of the fifth example has a peak wavelength in a wavelength range of 790 nm to 820 nm or a wavelength range of 905 nm to 970 nm.

Regarding Switching of Observation Light

As the types of light sources, a laser light source, a xenon light source, or a light-emitting diode (LED) light source, or an appropriate combination thereof may be adopted. It is preferable that the types of light sources, the wavelengths, the presence or absence of a filter, and the like are configured according to the types of objects, the purpose of observation, and the like. Further, it is preferable that the wavelengths of illumination light are combined and/or switched according to the types of objects, the purpose of observation, and the like at the time of observation. In a case where the wavelengths are to be switched, for example, a disc-shaped filter (rotary color filter) provided with filters, which are disposed in front of a light source and transmit or block light having specific wavelengths, may be rotated to switch the wavelength of light to be applied.

The imaging element used in the electronic endoscope is not limited to a color imaging element where a color filter is provided for each pixel, and may be a monochromatic imaging element. In a case where a monochromatic imaging element is used, imaging can be performed in order of surface (in order of color) while the wavelengths of illumination light are sequentially switched. For example, the wavelengths of illumination light to be emitted may be sequentially switched among violet, blue, green, and red; and broadband light (white light) may be applied and the wavelengths of illumination light to be emitted may be switched by the rotary color filter (red, green, blue, and the like). Further, one or a plurality of rays of narrow-band light may be applied and the wavelengths of illumination light to be emitted may be switched by the rotary color filter. The narrow-band light may be infrared light having two or more different wavelengths.

Generation Example of Special Light Image

The processor device 200 may generate a special light image having information on the specific wavelength range on the basis of a normal light image captured using white light. Here, the generation includes the concept of "acquisition". In this case, the processor device 200 functions as a special light image acquisition unit. The processor device 200 can acquire a signal in the specific wavelength range by performing an arithmetic operation based on color information about red (R), green (G), and blue (B) or cyan (C), magenta (M), and yellow (Y) included in the normal light image.

Generation Example of Feature Quantity Image

The processor device 200 may generate the feature quantity image using an arithmetic operation based on at least any one of the normal light image obtained from the application of light in a white-light wavelength range or light in a plurality of wavelength ranges as the light in a white-light wavelength range or the special light image obtained from the application of light in a specific wavelength range, as the medical image. The feature quantity image is a form of the medical image.

Illumination Using Phosphor

The phosphor may be disposed between the emission end of the light guide 170 and the illumination lenses 123A and 123B of the endoscope scope 100. For example, the blue laser light passing through the light guide 170 is applied to the phosphor to cause the phosphor to be in an excited state, and a part of the blue laser light transmitted through the phosphor and is emitted from the illumination lenses 123A and 123B as blue light.

The phosphor is excited by the blue laser light, and emits light in a wide range (yellow as color) from the wavelength range around the boundary between blue and green to the red wavelength range in the light wavelength range. The yellow light and the blue light transmitted through the phosphor are mixed to become white light, and the white light passes through the illumination lenses 123A and 123B to illuminate the object. The blue light transmitted through the phosphor also includes a part of the blue light emitted by the phosphor.

The phosphor may have properties of emitting yellow light in a case of receiving the application of blue laser light having a wavelength of 445 nm and transmitting blue light having a wavelength of 445 nm, but transmitting most of the blue laser light in a case of receiving the application of blue laser light having a wavelength of 405 nm. By using such a phosphor, it is possible to control the ratio of the blue light transmitted through the phosphor and the yellow light emitted by the phosphor by controlling the mixing ratio of the blue laser light having a wavelength of 445 nm and the blue laser light having a wavelength of 405 nm in the light source device.

Modification Example 1

In the above embodiments, an example of using the endoscope scope 100 as the flexible endoscope has been described, but the endoscope that images the inside of the body is not limited to the flexible endoscope, and may be a rigid endoscope or a capsule endoscope. The medical image handled by the medical image processing device according to the present disclosure is not limited to the endoscopic image, and may be an image generated by other medical image capturing devices such as an ultrasound diagnostic apparatus. The medical image capturing device may be at least one of X-ray imaging device, a computed tomography (CT) imaging device, a magnetic resonance imaging (MRI) device, or a nuclear medicine diagnostic apparatus. The technology of the present disclosure can be applied to devices that process medical images acquired using the various medical image capturing devices (modalities).

Modification Example 2

The medical image processing device of the present disclosure can be used as the diagnosis support apparatus that supports medical examination, treatment, or diagnosis by a doctor or the like. The term of "diagnosis support" includes the concept of medical examination support, treatment support, and lesion discrimination support.

Application Example to Medical Information Management System

The medical image processing device according to the present disclosure is not limited to the form applied to the processor device 200 of the endoscope system 10 illustrated in FIG. 1, and various applications are possible. For example, the medical image processing device can be applied to a medical information management system that manages various kinds of medical information including the endoscopic image.

An information management device in which processing functions of the medical image processing device according to the present disclosure are implemented may be installed, for example, in an operating room, an examination room, a conference room, or the like in a hospital, or may be installed in a medical institution or a research institution in an out-of-hospital facility. The information management device may be a workstation that supports medical examination, treatment, diagnosis, and the like, or may be a work support device that supports medical work. The work support device may comprise functions of accumulating clinical information, supporting preparation of diagnostic documents, supporting report creation, and the like.

Regarding Program Causing Computer to Realize Function of Medical Image Processing Device A program that causes a computer to realize the functions of the medical image processing devices 20, 20B, and 20C described in the above embodiments can be recorded on a computer-readable medium as a tangible non-temporary information storage medium such as an optical disk, a magnetic disk, or a semiconductor memory, and the program can be provided via the information storage medium. Further, instead of the form in which the program is provided by being stored in the tangible non-temporary information storage medium, a program signal can be provided as a download service using an electric telecommunication line such as the Internet.

Further, a part or all of the functions of the medical image processing devices described in the above embodiments can be provided as an application server, and a service that provides the processing functions via an electric telecommunication line can be performed.

Regarding Combination of Embodiments and Modification Examples

The constituents described in the above embodiments and the constituents described in the modification examples can be combined to be used as appropriate, and some constituents can be replaced.

Additional Remark

The present specification includes the disclosure of the invention described below in addition to the above-described embodiments and modification examples.

Additional Remark 1

A medical image processing device comprising: a medical image analysis processing unit that detects a region of interest, which is a region to be noticed, on the basis of a feature quantity of pixels of a medical image, and a medical image analysis result acquisition unit that acquires an analysis result of the medical image analysis processing unit.

The medical image analysis processing unit may include an image recognition unit.

Additional Remark 2

The medical image processing device, wherein the medical image analysis processing unit detects presence or absence of an object to be noticed, on the basis of the feature quantity of the pixels of the medical image, and the medical image analysis result acquisition unit acquires an analysis result of the medical image analysis processing unit.

Additional Remark 3

The medical image processing device, wherein the medical image analysis result acquisition unit acquires the analysis result of the medical image from a recording device which records the analysis result, and the analysis result includes any one or both of the region of interest that is the region to be noticed included in the medical image and presence or absence of the object to be noticed.

Additional Remark 4

The medical image processing device, wherein the medical image is a normal light image that is obtained from the application of light in a white-light wavelength range or light in a plurality of wavelength ranges as the light in a white-light wavelength range.

Additional Remark 5

The medical image processing device, wherein the medical image is an image that is obtained from the application of light in a specific wavelength range, and the specific wavelength range is a range narrower than the white-light wavelength range.

Additional Remark 6

The medical image processing device, wherein the specific wavelength range is a blue-light wavelength range or a green-light wavelength range of a visible-light wavelength range.

Additional Remark 7

The medical image processing device, wherein the specific wavelength range includes a wavelength range of 390 nm to 450 nm or 530 nm to 550 nm, and light in the specific wavelength range has a peak wavelength in a wavelength range of 390 nm to 450 nm or 530 nm to 550 nm.

Additional Remark 8

The medical image processing device, wherein the specific wavelength range is a red-light wavelength range of a visible-light wavelength range.

Additional Remark 9

The medical image processing device, wherein the specific wavelength range includes a wavelength range of 585 nm to 615 nm or 610 nm to 730 nm, and light in the specific wavelength range has a peak wavelength in a wavelength range of 585 nm to 615 nm or 610 nm to 730 nm.

Additional Remark 10

The medical image processing device, wherein the specific wavelength range includes a wavelength range where a light absorption coefficient in oxyhemoglobin is different from that in reduced hemoglobin, and light in the specific wavelength range has a peak wavelength in a wavelength range where a light absorption coefficient in oxyhemoglobin is different from that in reduced hemoglobin.

Additional Remark 11

The medical image processing device, wherein the specific wavelength range includes a wavelength range of $400\pm10$ nm, $440*10$ nm, $470\pm0$ nm, or 600 nm to 750 nm, and light in the specific wavelength range has a peak wavelength in a wavelength range of $400\pm10$ nm, $440*10$ nm, $470\pm10$ nm, or 600 nm to 750 nm.

Additional Remark 12

The medical image processing device, wherein the medical image is an in-vivo image of the inside of a living body, and the in-vivo image has information on fluorescence emitted by fluorescent materials in the living body.

Additional Remark 13

The medical image processing device, wherein the fluorescence is obtained from the application of excitation light, which has a peak wavelength in a range of 390 nm to 470 nm, to the inside of the living body.

Additional Remark 14

The medical image processing device, wherein the medical image is an in-vivo image of the inside of a living body, and the specific wavelength range is an infrared wavelength range.

Additional Remark 15

The medical image processing device, wherein the specific wavelength range includes a wavelength range of 790 nm to 820 nm or 905 nm to 970 nm, and light in the specific wavelength range has a peak wavelength in a wavelength range of 790 nm to 820 nm or 905 nm to 970 nm.

Additional Remark 16

The medical image processing device, wherein a medical image acquisition unit comprises a special light image acquisition unit that acquires a special light image having information about the specific wavelength range on the basis of a normal light image obtained from the application of light in a white-light wavelength range or light in a plurality of wavelength ranges as the light in a white-light wavelength range, and the medical image is the special light image.

Additional Remark 17

The medical image processing device, wherein a signal in the specific wavelength range is obtained from an arithmetic operation based on color information about RGB or CMY included in the normal light image.

Additional Remark 18

The medical image processing device further comprising: a feature quantity image generation unit generating a feature quantity image from an arithmetic operation based on at least one of the normal light image that is obtained from the application of light in a white-light wavelength range or light in a plurality of wavelength ranges as the light in a white-light wavelength range and the special light image that is obtained from the application of light in a specific wavelength range, wherein the medical image is the feature quantity image.

Additional Remark 19

An endoscope device comprising: the medical image processing device according to any one of Additional remarks 1 to 18; and an endoscope that acquires an image from the application of at least one of light in a white-light wavelength range or light in the specific wavelength range.

Additional Remark 20

A diagnosis support apparatus comprising: the medical image processing device according to any one of Additional remarks 1 to 18.

Additional Remark 21

A medical service support apparatus comprising: the medical image processing device according to any one of Additional remarks 1 to 18.

Others

In the embodiments of the invention described above, configuration requirements can be changed, added, or deleted as appropriate in a range without departing from the gist of the invention. The invention is not limited to the embodiments described above, and many modifications are possible by a person with ordinary skill in the equivalent related art within the technical idea of the present invention.

EXPLANATION OF REFERENCES

10: endoscope system
18: endoscopic image
18A: video
18B: frame image
19: static image
20: medical image processing device
20B: medical image processing device
20C: medical image processing device
22: image acquisition unit
23: insertion position detection device
24, 25: site information acquisition unit
26: lesion detection unit
28: consistency determination unit
30: report mode decision unit
32: display control unit
34: table storage unit
40: screen
42: observation image display region
44: site information report region
46: lesion information report region
100: endoscope scope
102: hand operation part
104: insertion part
106: universal cable
108: light guide connector
112: soft portion
114: bendable portion
116: hard distal end portion
116A: distal end-side end face
123: illumination unit
123A, 123B: illumination lens
126: forceps port
130: imaging unit
132: imaging lens
134: imaging element
136: drive circuit
138: analog front end
140: angle knob
141: air/water supply button
142: suction button
143: function button
144: imaging button
170: light guide
200: processor device
202: image input controller
204: image processing unit
205: communication control unit
206: video output unit
207: storage unit
208: operation unit
209: sound processing unit
209A: speaker
210: CPU
211: ROM
212: RAM
222: processor
224: computer-readable medium
225: image input interface
226: image processing processor
227: communication interface
228: input/output interface
230: bus
234: input device
236: display device
240: diagnosis support program
244: site recognition module
246: lesion detection module
246A: region detection algorithm
246B: type classification algorithm
248: consistency determination algorithm
250: report mode decision algorithm
252: display control program
261: esophagus lesion detection unit
262: stomach lesion detection unit
263: duodenum lesion detection unit
271: esophagus lesion detection module
272: stomach lesion detection module
273: duodenum lesion detection module
300: light source device
310: light source
310B: blue light source
310G: green light source
310R: red light source
330: stop
340: condenser lens
350: light source control unit
400: monitor
500: image preservation server
TB: correspondence relationship table
BB: bounding box
LS: lesion
S12 to S24: step of processing performed by medical image processing device

What is claimed is:

1. A medical image processing device comprising:
at least one processor,
wherein the at least one processor
acquires a medical image,
acquires site information indicating a site of an object shown in the medical image, in a human body,
detects a lesion from the medical image to acquire lesion type information indicating a lesion type, determines presence or absence of a contradiction between the site information and the lesion type information, and decides a report mode of the site information and the lesion type information on the basis of a determination result; and a memory, wherein in the memory, a table representing a correspondence relationship between a plurality of types of sites and lesion types for each site is stored, and the at least one processor determines presence or absence of the contradiction between the site information and the lesion type information by using the table.

2. The medical image processing device according to claim 1, wherein in the memory, a command executed by the at least one processor is stored, and the at least one processor performs processing including acquisition of the medical image, acquisition of the site information, acquisition of the lesion type information, determination of presence or absence of the contradiction, and decision of the report mode by executing the command by the at least one processor.

3. The medical image processing device according to claim 1, wherein the at least one processor decides that both the site information and the lesion type information are reported in a case where it is determined that there is no contradiction between the site information and the lesion type information.

4. The medical image processing device according to claim 1, wherein the at least one processor decides that at least one of the site information or the lesion type information is not reported in a case where it is determined that there is a contradiction between the site information and the lesion type information.

5. The medical image processing device according to claim 1, wherein in a case where it is determined that there is a contradiction between the site information and the lesion type information, the at least one processor compares a reliability of the site information with a reliability of the lesion type information, and decides to report the information with a higher reliability and not to report the information with a lower reliability of the site information and the lesion type information.

6. The medical image processing device according to claim 1, wherein in a case where it is determined that there is a contradiction between the site information and the lesion type information, the at least one processor decides not to report the site information and decides to report the lesion type information.

7. The medical image processing device according to claim 1, wherein in a case where it is determined that there is a contradiction between the site information and the lesion type information, the at least one processor compares each of a reliability of the site information and a reliability of the lesion type information with a reference value, and decides not to report both the site information and the lesion type information in a case where both the reliability of the site information and the reliability of the lesion type information are equal to or less than the reference value.

8. The medical image processing device according to claim 1, wherein in a case where it is determined that there is a contradiction between the site information and the lesion type information, the at least one processor decides to report that the contradiction has occurred.

9. The medical image processing device according to claim 1, wherein the at least one processor acquires the site information by recognizing the site of the object from the medical image.

10. The medical image processing device according to claim 1, wherein the at least one processor
acquires the site information indicated by an inference result that is output from a first neural network by inputting the medical image to the first neural network, and acquires the lesion type information of the lesion present in the medical image by inference using an inference result that is output from a second neural network by inputting the medical image to the second neural network.

11. The medical image processing device according to claim 10, wherein the at least one processor
acquires a score indicating a reliability of the site information using the first neural network, and acquires a score indicating a reliability of the lesion type information using the second neural network.

12. The medical image processing device according to claim 1, wherein the at least one processor further generates a report control signal for realizing a report of the decided report mode.

13. The medical image processing device according to claim 12, wherein the report control signal includes a display signal for realizing a report by display using a display.

14. The medical image processing device according to claim 13, further comprising:

the display that performs display of information according to the report mode decided by the at least one processor.

15. The medical image processing device according to claim 1, wherein the at least one processor acquires the time-series medical image.

16. The medical image processing device according to claim 1, wherein the medical image is an endoscopic image captured using an endoscope.

17. The medical image processing device according to claim 1, wherein the site is an organ, and
the site information is information indicating a name of the organ.

18. An endoscope system comprising:
an endoscope scope;
at least one processor,
wherein the at least one processor
acquires an endoscopic image obtained by imaging an inside of a body using the endoscope scope, acquires site information indicating a site of an object shown in the endoscopic image, in a human body, detects a lesion from the endoscopic image to acquire lesion type information indicating a lesion type, determines presence or absence of a contradiction between the site information and the lesion type information, decides a report mode of the site information and the lesion type information on the basis of a determination result, and generates a report control signal for executing a report according to the decided report mode; and a memory, wherein in the memory, a table representing a correspondence relationship between a plurality of types of sites and lesion types for each site is stored, and the at least one processor determines presence or absence of the contradiction between the site information and the lesion type information by using the table.

19. A diagnosis support method performed by at least one processor and a memory, comprising:

acquiring a medical image;

acquiring site information indicating a site of an observation target included in the medical image, in a human body;

detecting a lesion from the medical image to acquire lesion type information indicating a lesion type;

determining presence or absence of a contradiction between the site information and the lesion type information;

deciding a report mode of the site information and the lesion type information on the basis of a determination result; and displaying information on a display according to the decided report mode; and storing a table representing a correspondence relationship between a plurality of types of sites and lesion types for each site in the memory, wherein presence or absence of the contradiction between the site information and the lesion type information is determined by the at least one processor through using the table.

20. A non-transitory, computer-readable tangible recording medium which records computer instructions that, when read by a computer, cause the computer to realize:

a function of acquiring a medical image;

a function of acquiring site information indicating a site of an object shown in the medical image, in a human body;

a function of detecting a lesion from the medical image to acquire lesion type information indicating a lesion type;

a function of determining presence or absence of a contradiction between the site information and the lesion type information;

a function of deciding a report mode of the site information and the lesion type information on the basis of a determination result; and a function of storing a table representing a correspondence relationship between a plurality of types of sites and lesion types for each site, wherein presence or absence of the contradiction between the site information and the lesion type information is determined by using the table.

* * * * *